E

(12) United States Patent
Jain et al.

(10) Patent No.: US 9,023,879 B2
(45) Date of Patent: May 5, 2015

(54) SPECIFIC DIARYLHYDANTOIN AND DIARYLTHIOHYDANTOIN COMPOUNDS

(71) Applicants: Rajendra Parasmal Jain, Pune (IN); Jacqueline A. Gibbons, Piedmont, CA (US)

(72) Inventors: Rajendra Parasmal Jain, Pune (IN); Jacqueline A. Gibbons, Piedmont, CA (US)

(73) Assignee: Medivation Prostate Therapeutics, Inc., San Francisco, CA (US)

(*) Notice: Subject to any disclaimer, the term of this patent is extended or adjusted under 35 U.S.C. 154(b) by 0 days.

(21) Appl. No.: 13/925,507

(22) Filed: Jun. 24, 2013

(65) Prior Publication Data

US 2013/0331421 A1    Dec. 12, 2013

Related U.S. Application Data

(63) Continuation of application No. 13/202,970, filed as application No. PCT/US2010/025283 on Feb. 24, 2010, now Pat. No. 8,524,755.

(60) Provisional application No. 61/156,398, filed on Feb. 27, 2009, provisional application No. 61/155,119, filed on Feb. 24, 2009.

(51) Int. Cl.
| | | |
|---|---|---|
| *A61K 31/4166* | (2006.01) | |
| *C07D 233/72* | (2006.01) | |
| *C07D 233/86* | (2006.01) | |
| *C07D 233/74* | (2006.01) | |
| *C07D 233/84* | (2006.01) | |

(52) U.S. Cl.
CPC .......... *C07D 233/86* (2013.01); *A61K 31/4166* (2013.01); *C07D 233/74* (2013.01); *C07D 233/84* (2013.01); *C07D 233/72* (2013.01)

(58) Field of Classification Search
USPC ........................................ 514/389; 548/317.1
See application file for complete search history.

(56) References Cited

U.S. PATENT DOCUMENTS

| | | |
|---|---|---|
| 3,846,441 A | 11/1974 | Mine et al. |
| 2005/0154028 A1 | 7/2005 | Bromidge et al. |
| 2007/0004753 A1 | 1/2007 | Sawyers et al. |
| 2007/0135492 A1 | 6/2007 | Lange et al. |
| 2008/0139634 A2 | 6/2008 | Jung et al. |

FOREIGN PATENT DOCUMENTS

| | | | |
|---|---|---|---|
| EP | 1790640 A1 | 5/2007 | |
| JP | 2008-511114 A | 4/2008 | |
| RU | 2152934 C1 | 7/2000 | |
| WO | WO 2006/124118 | 11/2006 | |
| WO | WO-2006/1214118 A1 * | 11/2006 | ......... A61K 31/4184 |
| WO | 2007127010 A2 | 11/2007 | |

OTHER PUBLICATIONS

International Preliminary Report on Patentability and Written Opinion in PCT/US10/025283 mailed Aug. 30, 2011.
International Search Report in PCT/US10/025283 mailed Apr. 14, 2010.

* cited by examiner

*Primary Examiner* — Kamal Saeed
*Assistant Examiner* — Janet L Coppins
(74) *Attorney, Agent, or Firm* — Banner & Witcoff, Ltd.

(57) ABSTRACT

Compositions, such as pharmaceutical compositions, comprising specific diarylhydantoin and diarylthiohydantoin compounds, or salts or solvates thereof, are provided. Isolated and purified forms of the compounds are also described, as are unit dosage forms, compositions of substantially pure compound and kits comprising the compounds. The compounds and pharmaceutical compositions thereof may find use in the prevention and/or treatment of a variety of conditions, including prostate cancer, Parkinson's disease, Alzheimer's disease, and others.

17 Claims, No Drawings

SPECIFIC DIARYLHYDANTOIN AND DIARYLTHIOHYDANTOIN COMPOUNDS

CROSS-REFERENCE TO RELATED APPLICATIONS

This is a continuation of Ser. No. 13/202,970 filed as a national stage application of PCT/US2010/025283 filed on Feb. 24, 2010, which claims priority to Ser. No. 61/155,119 filed on Feb. 24, 2009 and Ser. No. 61/156,398 filed on Feb. 27, 2009. Each of these applications is incorporated herein by reference in its entirety.

STATEMENT REGARDING FEDERALLY SPONSORED RESEARCH OR DEVELOPMENT

Not applicable.

FIELD OF THE INVENTION

Provided herein are three specific diarylhydantoin and two specific diarylthiohydantoin compounds, and pharmaceutical compositions and other forms comprising these five specific compounds. Also provided are methods for preventing and/or treating conditions in mammals such as Parkinson's disease, Alzheimer's disease, and prostate cancer.

BACKGROUND OF THE INVENTION

Diarylhydantoin compounds, including diarylthiohydantoin compounds, have been described in U.S. Publication Nos. 2007/0004753, 2007/0254933 and 2009/0111864. Nevertheless, there remains a need for new therapies for the treatment of various diseases, including prostate cancer. New therapies for the treatment of Parkinson's disease and Alzheimer's disease are also sought.

(MI)-(MV) as detailed herein are metabolites of compound RD162' disclosed in U.S. Publication No. 2007/0004753 and may find use in therapy.

BRIEF SUMMARY OF THE INVENTION

Compounds (MI)-(MV) are described. Formula (I) as provided herein describes and intends compounds of the formula (MI)-(MV). Compound (MI) effects through the norepinephrine transporter. Norepinephrine transporter modulators have been useful in therapies for the treatment of depression, Alzheimer's disease, attention deficit disorders and Parkinson's disease. Compound (MII) effects via the progesterone receptor. Progesterone receptor modulators have been used in therapies in which progesterone is implicated. Progesterone receptor modulators have potential for use in birth control either to prevent pregnancy or to abort pregnancy. Compound (MIV) effects on the sigma receptor. Sigma receptor modulators have been useful in therapies for treating depression. Compounds (MI)-(MV) are metabolites of compound RD162'. RD162' has found use in treating prostate cancer.

Methods and compositions are also described. In one variation, the method comprises administering a compound of formula (MI), (MII), (MIII), (MIV) or (MV) to an individual in an amount effective to modulate a receptor, such as a receptor listed in Tables 5 and 9. Methods of isolating a compound of formula (MI), (MII), (MIII), (MIV) or (MV) are detailed herein. Methods of using a compound of formula (MI), (MII), (MIII), (MIV) or (MV) in therapy are also provided. In one aspect, the therapy is the treatment of Parkinson's disease, Alzheimer's disease or prostate cancer. Pharmaceutical compositions comprising a compound of formula (MI), (MII), (MIII), (MIV) or (MV) and a pharmaceutically acceptable carrier are also embraced, as are isolated and/or purified forms of a compound of formula (MI), (MII), (MIII), (MIV) or (MV). Unit dosage forms of a compound of formula (MI), (MII), (MIII), (MIV) or (MV) are also described.

Accordingly, in one aspect, compounds are provided that are of the formula (I):

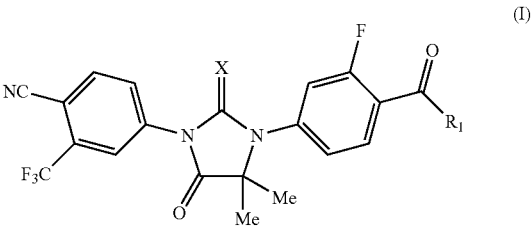

(I)

wherein:

X is S or O, and when X is S, then $R^1$ is OH or $NH_2$; and when X is O then $R^1$ is OH, $NH_2$ or NHMe, or a pharmaceutically acceptable salt or solvate thereof.

Thus, compounds of the formulae (MI), (MII), (MIII), (MIV) and (MV):

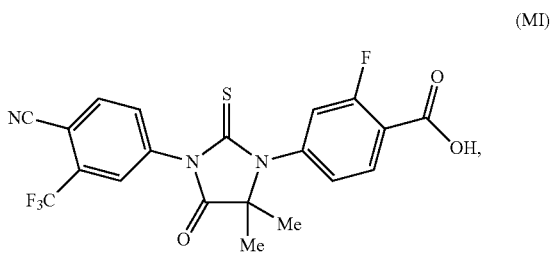

(MI)

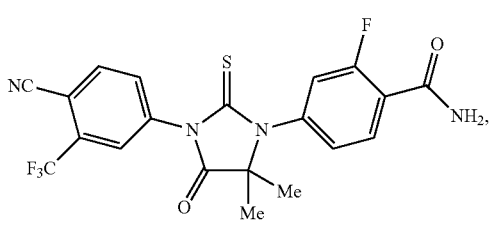

(MII)

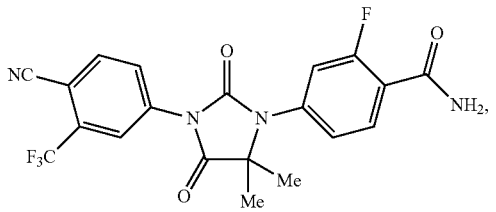

(MIII)

(MIV)

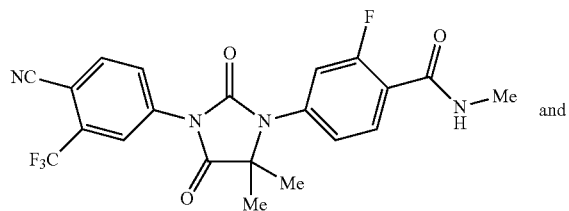

and (MV)

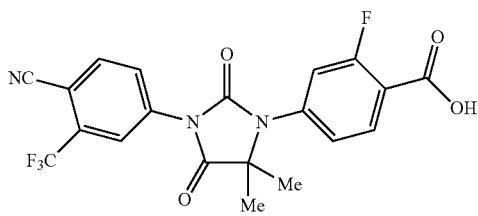

are described. It is understood that salts of the compounds, such as pharmaceutically acceptable salts, are also provided.

Compounds of the formula (I) have been identified as metabolites of the compound RD162', which has been found useful in treating prostate cancer and is described in US application publication No. 2007/0004753. As described in the Examples below, RD162' and metabolites thereof were isolated by acetonitrile-induced protein precipitation of 100 μL of plasma. Metabolites were identified by scanning measurements of time-of-flight for positive ions from 55 to 800 amu. A particular molecule was identified as a potential RD162' metabolite if its fragmentation yielded subspecies having a pattern consistent with that of parent RD162'. Five putative metabolites were present in plasma from rats, dogs, and/or humans: (MI), (MII), (MIII), (MIV) and (MV). The structures of the metabolites were deduced by analysis of the mass spectra and the putative metabolites were then synthesized. The molecular structures of the metabolites were confirmed through an LC/MS/MS co-elution experiment in which the synthesized molecules were directly compared to the structures isolated from rat, dog, and human plasma samples.

Compounds of the formula (I) may also find use in therapy, e.g., in the treatment of prostate cancer or in the treatment of other indications commensurate with the activity of such compounds, such as the receptor binding activity detailed herein.

In one embodiment, with respect to the compounds of formula (I) (i.e., compounds (MI)-(MV)), the compounds are provided in substantially pure form.

In one aspect, compositions comprising the compounds are provided, wherein the composition is free of blood or other body fluids.

In another aspect, pharmaceutical compositions are provided comprising a compound of formula (I), and a pharmaceutically acceptable carrier. The pharmaceutical composition can comprise one or more of the compounds described herein, or salts or solvates thereof.

In another aspect, methods are provided for preventing or treating a condition from among those listed herein, and particularly, such condition as may be associated with, e.g., depression, memory dysfunctions such as Alzheimer's disease and Parkinson's disease, and prostate cancer, which method comprises administering to an individual in need thereof a therapeutically effective amount of a compound of the formula (I), or a salt or solvate thereof, or pharmaceutical composition comprising the foregoing.

The invention also embraces the use of any of the compounds of the invention for the preparation of medicaments, which may be administered for therapy, such as for the treatment of indications disclosed herein, including prostate cancer.

In additional aspects, methods are provided for synthesizing the compounds described herein, with representative synthetic protocols and pathways described below.

A pharmaceutical composition comprising (a) a compound of the formula (I):

(I)

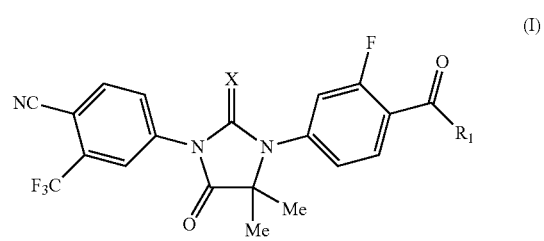

wherein:

X is S or O, and when X is S then $R^1$ is OH or $NH_2$; and when X is O then $R^1$ is OH, $NH_2$ or NHMe;

or a pharmaceutically acceptable salt or solvate thereof, and (b) a pharmaceutically acceptable carrier are provided. In one aspect of formula (I), X is S and $R^1$ is OH or $NH_2$. In another aspect of formula (I), X is O and $R^1$ is OH, $NH_2$ or NHMe. In a particular variation of formula (I), the compound is of the formula (MI):

MI

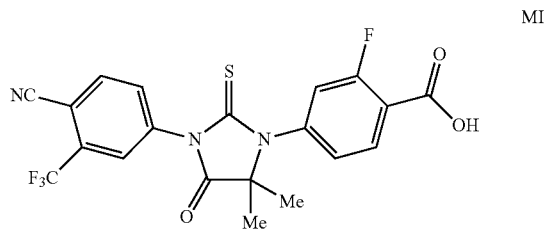 [SMILES: CC1(C)C(=O)N(c2ccc(C#N)c(C(F)(F)F)c2)C(=S)N1c1ccc(C(=O)O)c(F)c1]

or a pharmaceutically acceptable salt or solvate thereof. In another variation of formula (I), the compound is of the formula (MII):

MII

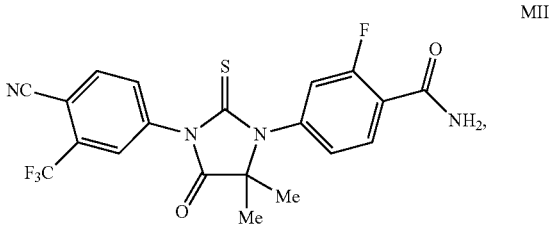 [SMILES: CC1(C)C(=O)N(c2ccc(C#N)c(C(F)(F)F)c2)C(=S)N1c1ccc(C(N)=O)c(F)c1]

or a pharmaceutically acceptable salt or solvate thereof. In still a further variation of formula (I), the compound is of the formula (MIII):

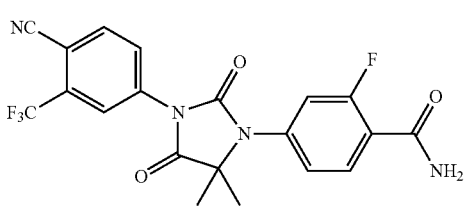

(MIII)

or a pharmaceutically acceptable salt or solvate thereof. In yet another variation of the formula (I), the compound is of the formula (MIV):

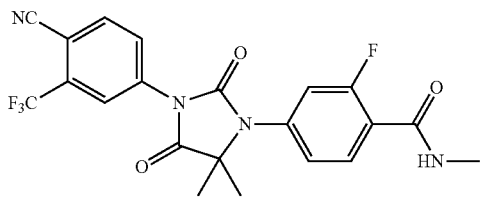

(MIV)

or a pharmaceutically acceptable salt or solvate thereof. In still another variation of the formula (I), the compound is of the formula (MV):

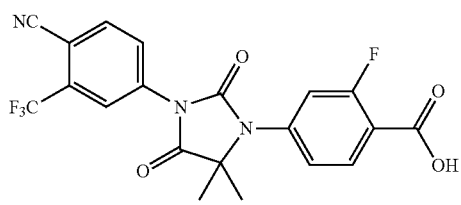

(MV)

or a pharmaceutically acceptable salt or solvate thereof.

A composition of substantially pure compound is also provided, wherein the compound is of the formula I:

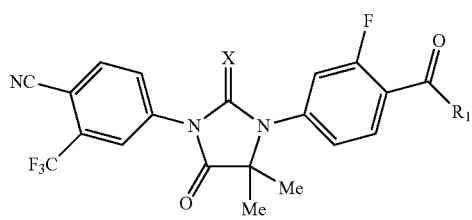

(I)

wherein:

X is S or O, and when X is S then $R^1$ is OH or $NH_2$; and when X is O then $R^1$ is OH, $NH_2$ or NHMe;

or a salt or solvate thereof. In one aspect of formula (I), X is S and $R^1$ is OH or $NH_2$. In another aspect of formula (I), X is O and $R^1$ is OH or $NH_2$. In a particular variation of formula (I), the compound is of the formula (MI):

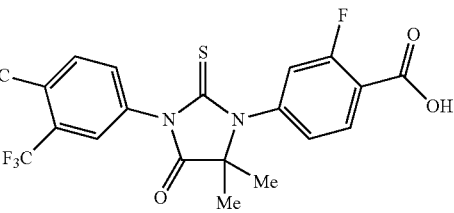

MI or a salt or solvate thereof. In another variation of formula (I), the compound is of the formula (MII):

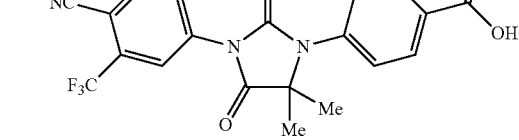

MII or a salt or solvate thereof. In still a further variation of formula (I), the compound is of the formula (MIII):

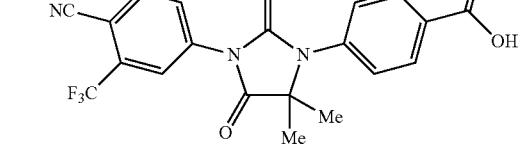

(MIII)

or a salt or solvate thereof. In yet another variation of the formula (I), the compound is of the formula (MIV):

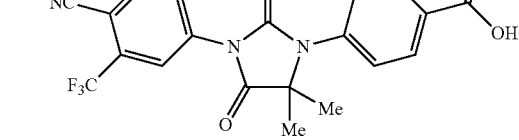

(MIV)

or a salt or solvate thereof. In still another variation of the formula (I), the compound is of the formula (MV):

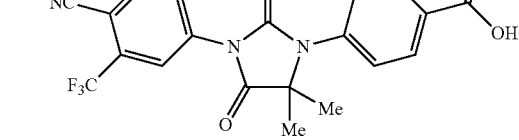

(MV)

or a salt or solvate thereof. A composition of any of the preceding embodiments and variations is also provided, wherein the composition contains less than about 10 weight percent impurity.

The invention also embraces a method of administering a compound of the formula (I):

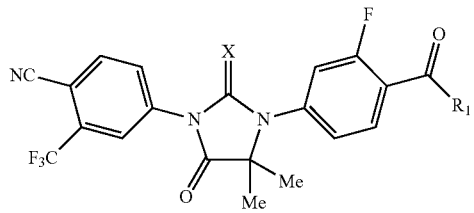
(I)

wherein:
X is S or O, and
when X is S then $R^1$ is OH or $NH_2$; and
when X is O then $R^1$ is OH, $NH_2$ or NHMe;
or a pharmaceutically acceptable salt or solvate thereof, to an individual for therapy. In one aspect of formula (I), X is S and $R^1$ is OH or $NH_2$. In another aspect of formula (I), X is O and $R^1$ is OH, $NH_2$ or NHMe. In a particular embodiment, the therapy is the treatment of prostate cancer. In another embodiment, the therapy is the treatment of Parkinson's disease or Alzheimer's disease.

Also provided is a kit comprising a compound of the formula (I):

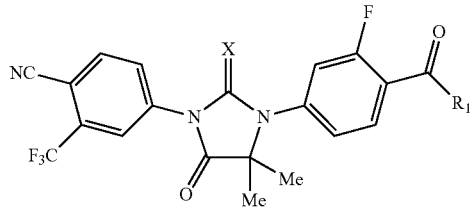
(I)

wherein:
X is S or O, and
when X is S then $R^1$ is OH or $NH_2$; and
when X is O then $R^1$ is OH, $NH_2$ or NHMe;
or a pharmaceutically acceptable salt or solvate thereof. In a particular variation, X is S and $R^1$ is OH or $NH_2$. In another variation, X is O and $R^1$ is OH, $NH_2$ or NHMe. In one embodiment, the kit further comprises instructions for use, which in one variation are instructions for use of the compound in the treatment of prostate cancer or instructions for use of the compound in the treatment of Parkinson's disease or Alzheimer's disease.

Also provided herein is a unit dosage form comprising a compound of the formula (I):

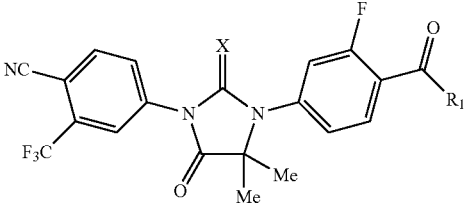
(I)

wherein:
X is S or O, and
when X is S then $R^1$ is OH or $NH_2$; and
when X is O then $R^1$ is OH, $NH_2$ or NHMe;
or a pharmaceutically acceptable salt or solvate thereof. In one embodiment, X is S and $R^1$ is OH or $NH_2$. In another embodiment, X is O and $R^1$ is OH, $NH_2$ or NHMe.

Also provided is an isolated compound of the formula (I):

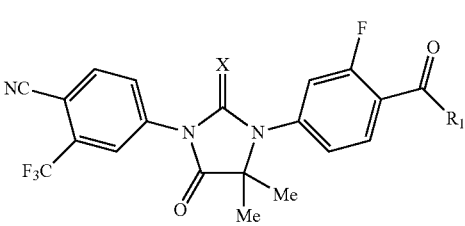
(I)

wherein:
X is S or O, and
when X is S then $R^1$ is OH or $NH_2$; and
when X is O then $R^1$ is OH, $NH_2$ or NHMe;
or a pharmaceutically acceptable salt or solvate thereof. In one aspect, X is S and $R^1$ is OH or $NH_2$. In another aspect, X is O and $R^1$ is OH, $NH_2$ or NHMe.

Other objects and advantages will become apparent to those skilled in the art from a consideration of the ensuing detailed description.

DETAILED DESCRIPTION OF THE INVENTION

Definitions

Unless clearly indicated otherwise, the terms "a," "an," and the like, refer to one or more.

Reference to "about" a value or parameter herein includes (and describes) embodiments that are directed to that value or parameter per se. For example, description referring to "about X" includes description of "X".

As used herein, by "pharmaceutically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. A pharmaceutically acceptable salt intends ionic interactions and not a covalent bond. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" is used interchangeably with "carrier" herein and as used herein intends an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Unless clearly indicated otherwise, "an individual" as used herein intends a mammal, including but not limited to a human, bovine, primate, equine, canine, feline, porcine, and ovine animals. Thus, the invention finds use in both human medicine and in the veterinary context, including use in agricultural animals and domestic pets.

The term "effective amount" or "therapeutically effective amount" intends such amount of a compound which should be effective in a given therapeutic form. As is understood in the art, an effective amount may be in one or more doses, e.g., a single dose or multiple doses may be required to achieve the desired treatment endpoint. Standard methods can be used to measure the magnitude of this effect, such as in vitro assays with purified enzyme, cell-based assays, animal models, or human testing.

As used herein, "treatment" or "treating" is an approach for obtaining a beneficial or desired result, including clinical results. For purposes of this invention, beneficial or desired clinical results include, but are not limited to, alleviation of a symptom and/or diminishment of the extent of a symptom and/or preventing a worsening of a symptom associated with a disease or condition.

As used herein, a compound that is a receptor "modulator" intends and encompasses a compound that binds to or inhibits binding of a ligand to the receptor or reduces or eliminates or increases or enhances or mimics an activity of the receptor. As such, a "receptor modulator" encompasses both a receptor antagonist and a receptor agonist.

As used herein, "unit dosage form" refers to physically discrete units, suitable as unit dosages, each unit containing a predetermined quantity of active ingredient calculated to produce the desired therapeutic effect in association with the required pharmaceutical carrier.

A composition of "substantially pure" compound intends that the composition contains less than about 35% or less than about 20% or less than about 15% or preferably less than about 10% or more preferably less than about 5% or even more preferably less than about 3% and most preferably less than about 1% impurity.

It is understood that wherever embodiments are described herein with the language "comprising," otherwise analogous embodiments described in terms of "consisting of" and/or "consisting essentially of" are also provided.

Compounds and Compositions

In certain aspects, provided herein are compounds and compositions comprising such compounds, e.g., as pharmaceutical compositions. The compounds and compositions may find use in therapy, e.g., in the treatment of prostate cancer, Parkinson's disease or Alzheimer's disease. Compositions of substantially pure compounds are also provided, as are isolated and synthetic compounds. Unit dosage forms of the compounds are also provided.

Methods of isolating a compound of formula (MI), (MII), (MIII), (MIV) and/or (MV) are detailed herein, such as method of isolating the compounds from blood or other body fluid. Pharmaceutical compositions comprising a compound of formula (MI), (MII), (MIII), (MIV) or (MV) and a pharmaceutically acceptable carrier are also embraced, as are isolated and/or purified forms of a compound of formula (MI), (MII), (MIII), (MIV) or (MV).

In one aspect of the invention, compounds of the formulae (MI), (MII), (MIII) and (MIV) and salts thereof are described. A compound of the formula (MV) is also provided. A compound of formula (MI), (MII), (MIII) or (MIV) may be in isolated form and compositions comprising isolated forms are embraced. Isolated forms of compound (MV) are also provided. A compound of formula (MI), (MII), (MIII) or (MIV) may be in a purified form and compositions comprising a compound in purified forms are detailed herein. Purified forms of compound (MV) and compositions comprising (MV) in purified form is also provided.

In one aspect, a composition comprising a compound of the formula (I) is provided, wherein the composition is free of blood or other body fluid. In one aspect, a composition comprising a purified form of a compound of the formula (I) is provided. Such a composition may contain other components, such as a pharmaceutically acceptable carrier. In another aspect, a composition of substantially pure form of a compound of formula (I) is provided, wherein the composition comprises less than about any of 15%, 10%, 5%, 3% and 1% impurity, which impurity may be, e.g., a compound not of the formula (I) or blood or other body fluid. In one aspect, a composition of substantially pure compound comprises only one of (MI), (MII), (MIII), (MIV) and (MV).

Compound (MI) is of the formula:

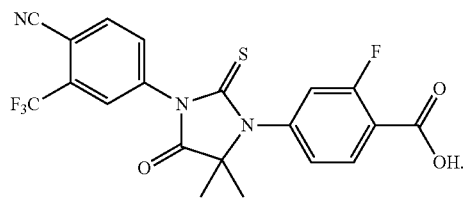
(MI)

Compound (MII) is of the formula:

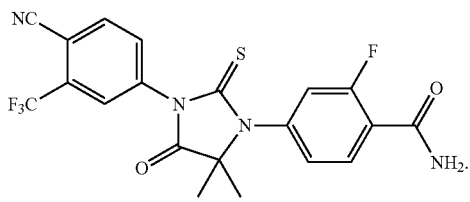
(MII)

Compound (MIII) is of the formula:

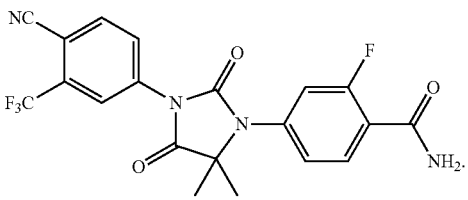
(MIII)

Compound (MIV) is of the formula:

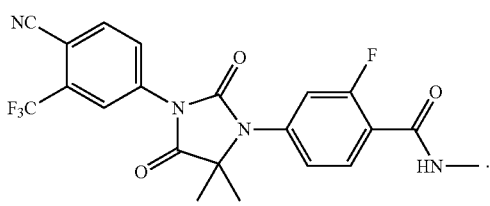
(MIV)

Compounds (MI)-(MIV) may be present as salts, such as pharmaceutically acceptable salts.

Compound (MV) is of the formula:

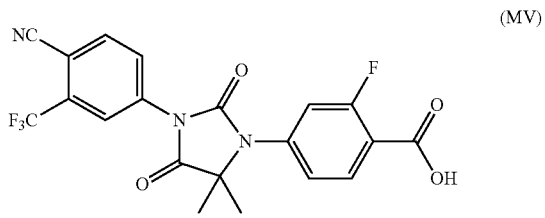
(MV)

and may also be present as a salt, such as a pharmaceutically acceptable salt.

In another aspect of the invention, compounds are provided that are of the formula (I):

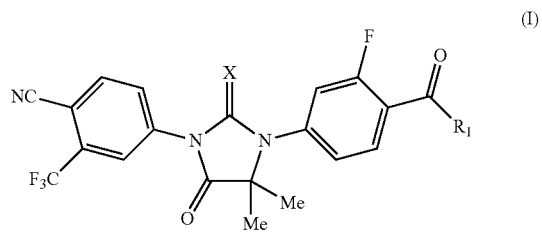
(I)

wherein:

X is S or O, and when X is S then $R^1$ is OH or $NH_2$; and when X is O then $R^1$ is OH, $NH_2$ or NHMe;

or a pharmaceutically acceptable salt or solvate thereof.

Thus, compounds according to formulae (MI), (MII), (MIII), (MIV) and (MV):

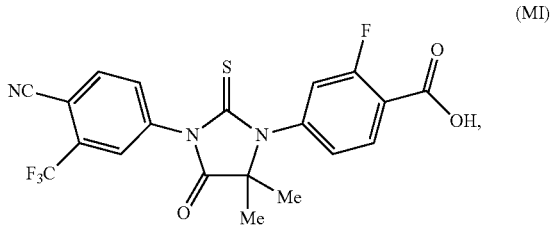 [SMILES: CC1(C)C(=O)N(c2ccc(C#N)c(C(F)(F)F)c2)C(=S)N1c1ccc(C(N)=O)c(F)c1]
(MI)

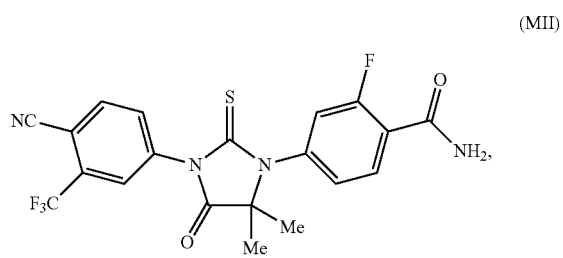
(MII)

(MIII)
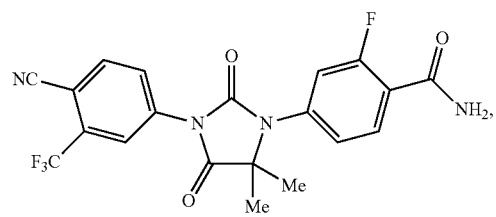

(MIV)
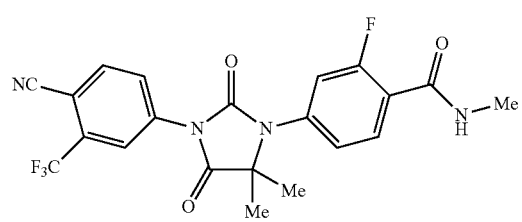 and (MV)
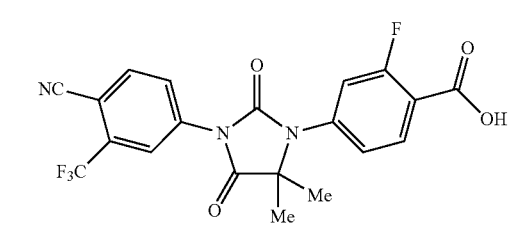

are provided and may be used in the compositions and methods described herein.

In one embodiment, with respect to the compounds of formula (I), X is S and R¹ is OH or NH₂. Thus, in one variation, compounds of formula (I) are of the formula (MI) or (MII):

(MI)
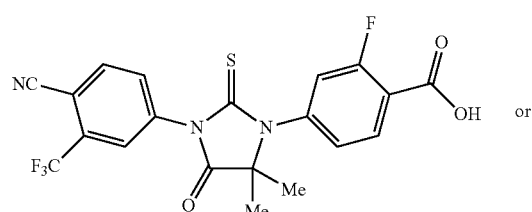 or (MII)
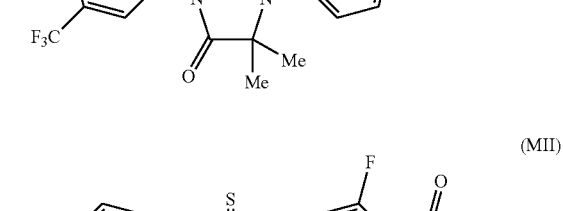

In another embodiment, with respect to the compounds of formula (I), X is O and R¹ is OH, NH₂ or NHMe. Thus, in one variation, compounds of formula (I) are of the formula (MIII), (MIV) or (MV):

(MIII)
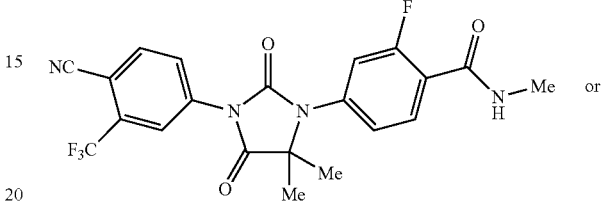

(MIV)
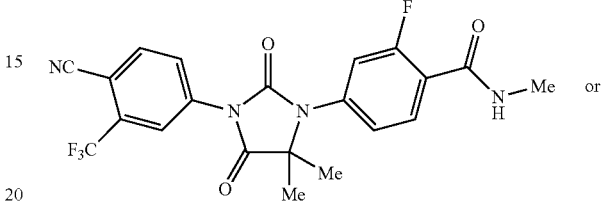 or (MV)

In one particular embodiment, with respect to the compounds of formula (I), X is S and R¹ is OH. Thus, in one variation, a compound of formula (I) is of the formula (MI):

MI
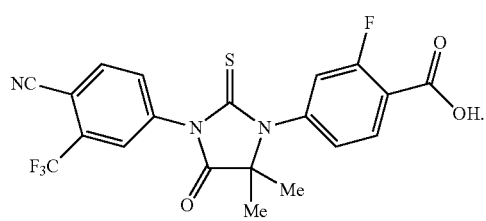

In another particular embodiment, with respect to the compounds of formula (I), X is S and R¹ is NH₂. Thus, in one variation, a compound of formula (I) is of the formula (MII):

MII
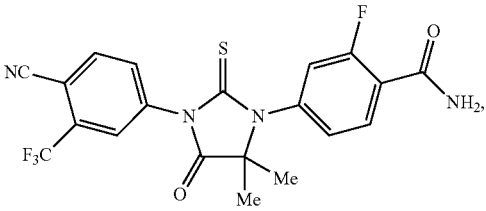

In yet another particular embodiment, with respect to the compounds of formula (I), X is O and R¹ is NH₂. Thus, in one variation, a compound of formula (I) is of the formula (MIII):

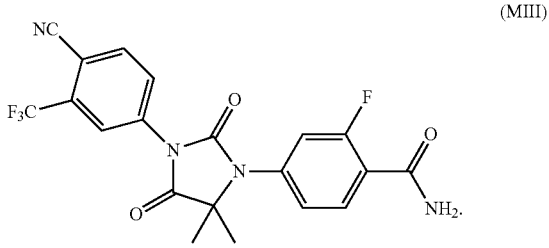 [SMILES: CC1(C)C(=O)N(c2ccc(C#N)c(C(F)(F)F)c2)C(=O)N1c1ccc(C(N)=O)c(F)c1]

(MIII)

In yet another particular embodiment, with respect to the compounds of formula (I), X is O and $R^1$ is NHMe. Thus, in one variation, a compound of formula (I) is of the formula (MIV):

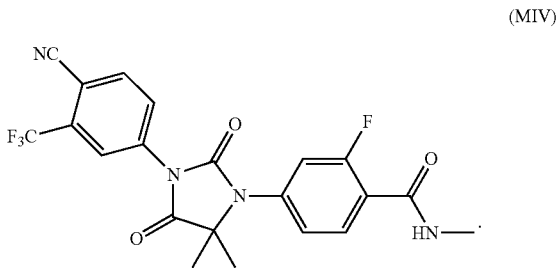 [SMILES: CNC(=O)c1ccc(N2C(=O)N(c3ccc(C#N)c(C(F)(F)F)c3)C(=O)C2(C)C)cc1F]

(MIV)

In yet another particular embodiment, with respect to the compounds of formula (I), X is O and $R^1$ is OH. Thus, in one variation, a compound of formula (I) is of the formula (MV):

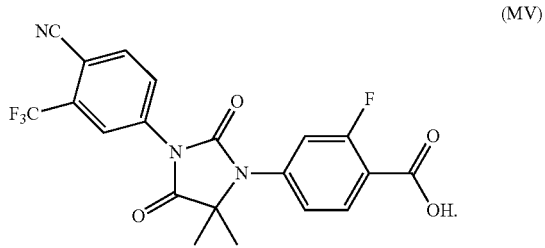 [SMILES: CC1(C)C(=O)N(c2ccc(C#N)c(C(F)(F)F)c2)C(=O)N1c1ccc(C(=O)O)c(F)c1]

(MV)

In another aspect of the invention, provided herein is a pharmaceutically acceptable salt of a compound according to formulae (MI), (MII), (MIII), (MIV) or (MV). In one embodiment, the pharmaceutically acceptable salt is of a compound according to formulae (MI) or (MII). In another embodiment, the pharmaceutically acceptable salt is of a compound according to formulae (MIII), (MIV), or (MV).

Compounds of the formulae (MI), (MII), (MIII), (MIV) and (MV) and salts thereof are described. Thus, compounds (MI)-(MV) may be present as salts, such as pharmaceutically acceptable salts. A compound of formula (MI), (MII), (MIII), (MIV) or (MV) may be in isolated form and compositions comprising isolated forms are embraced. A compound of formula (MI), (MII), (MIII), (MIV) or (MV) may be in a purified form and compositions comprising a compound in purified form are detailed herein.

A composition of substantially pure compound according to formulae (I), or salt thereof, is provided. In one aspect, the composition is a substantially pure composition of compound (MI) or (MII). In another aspect, a composition of substantially pure (MIII), (MIV) or (MV), or salt thereof, is described. The substantially pure compositions in one aspect contain less than about any of 10 weight percent or 5 weight percent or 1 weight percent impurity.

Thus, compositions comprising a compound of the formula (MI), (MII), (MIII), (MIV) or (MV) or a salt thereof are provided, such as compositions of substantially pure compounds. In some embodiments, a composition containing a compound of formula (MI), (MII), (MIII), (MIV) or (MV) or a salt thereof is in substantially pure form. In one variation, "substantially pure" intends a composition that contains less than about 35% impurity, wherein the impurity denotes a compound other than the compound of the formula (MI), (MII), (MIII), (MIV) or (MV) or a salt thereof. In one variation, a composition of substantially pure compound of the formula (MI), (MII), (MIII), (MIV) or (MV) or a salt thereof is provided wherein the composition contains less than about 25% impurity. In another variation, a composition of substantially pure compound of the formula (MI), (MII), (MIII), (MIV) or (MV) or a salt thereof is provided wherein the composition contains less than about 20% impurity. In still another variation, a composition of substantially pure compound of the formula (MI), (MII), (MIII), (MIV) or (MV) or a salt thereof is provided wherein the composition contains less than about 10% impurity. In a further variation, a composition of substantially pure compound of the formula (MI), (MII), (MIII), (MIV) or (MV) or a salt thereof is provided wherein the composition contains less than about 5% impurity. In another variation, a composition of substantially pure compound of the formula (MI), (MII), (MIII), (MIV) or (MV) or a salt thereof is provided wherein the composition contains less than about 3% impurity. In still another variation, a composition of substantially pure compound of the formula (MI), (MII), (MIII), (MIV) or (MV) or a salt thereof is provided wherein the composition contains less than about 1% impurity. In a further variation, a composition of substantially pure compound of the formula (MI), (MII), (MIII), (MIV) or (MV) or a salt thereof is provided wherein the composition contains less than about 0.5% impurity. In one aspect, % impurity intends percent impurity as determined by weight percent.

Pharmaceutical compositions are provided wherein the composition comprises a compound of the formula (MI), (MII), (MIII), (MIV) or (MV) or a salt thereof and a pharmaceutically acceptable carrier. In another aspect of the invention, provided herein is a pharmaceutical composition comprising a pharmaceutically acceptable carrier and a therapeutically effective amount of a compound according to formula (MI), (MII), (MIII), (MIV) or (MV), or a pharmaceutically acceptable salt or solvate thereof.

In one embodiment, with respect to the pharmaceutical composition, the carrier or excipient is suitable for parenteral administration. In one embodiment, with respect to the pharmaceutical composition, the carrier is suitable for oral administration. In one embodiment, with respect to the pharmaceutical composition, the carrier is suitable for topical administration.

In one embodiment, the pharmaceutical composition comprises a compound according to formula (MI) or (MII). In another embodiment, the pharmaceutical composition comprises a compound according to formulae (MIII), (MIV), or (MV). In one aspect, the pharmaceutical composition is free of a compound according to formula (MI) or (MII). In another aspect, the pharmaceutical composition is free of a compound according to formulae (MIII), (MIV), or (MV).

In one embodiment, a pharmaceutical composition of a substantially pure form of the compound according to formulae (MI) or (MII) is provided. In another embodiment, a pharmaceutical composition of a substantially pure form of the compound according to formulae (MIII), (MIV), or (MV) is provided.

A compound of the formula (I) may be formulated with suitable carriers for any available delivery route, including oral, mucosal (e.g., nasal, sublingual, vaginal, buccal or rectal), parenteral (e.g., intramuscular, subcutaneous, or intravenous), topical or transdermal delivery. A compound of the formula (I) may be formulated with suitable carriers to provide delivery forms that include, but are not limited to: tablets, caplets, capsules (such as hard gelatin capsules and soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

A pharmaceutical formulation may be prepared by combining a compound of the formula (I) as an active ingredient with a pharmacologically acceptable carrier, which are known in the art. Depending on the therapeutic form of the system (e.g., oral tablet), the carrier may be in various forms. In addition, pharmaceutical preparations may contain preservatives, solubilizers, stabilizers, re-wetting agents, emulgators, sweeteners, dyes, adjusters, buffers, coating agents or antioxidants. Preparations containing a compound of the formula (I) as the active ingredient may also contain other substances which have valuable therapeutic properties. Therapeutic forms may be represented by a usual standard dose and may be prepared by a known pharmaceutical method. Suitable formulations can be found, e.g., in *Remington's Pharmaceutical Sciences*, Mack Publishing Company, Philadelphia, Pa., $21^{st}$ ed. (2005), which is incorporated herein by reference.

The amount of a compound of the formula (I) in a pharmaceutical or other composition, including a unit dosage form, may be an effective amount. In one variation, a composition, such as a pharmaceutical composition, comprises a compound of the formula (I) in a dosage form in an amount of from about 10 ng to about 1,500 mg or more.

Articles of manufacture comprising a compound of the invention, or a salt or solvate thereof, in a suitable container are provided. The container may be a vial, jar, ampoule and the like.

The methods and kits provided herein may comprise a compound as detailed herein, or a salt or solvate thereof, the same as if each as every embodiment were specifically and individually listed. Likewise, the method and kits provided herein may comprise a composition as detailed herein, such as a pharmaceutical composition, the same as if each and every embodiment were specifically and individually listed.

Methods

Compounds of the formula (I) (i.e., compounds (MI)-(MV)) are active at one or more molecular targets and may thus find use in therapy. Compounds (MI)-(MV), or a salt or solvate thereof may be used to modulate a receptor of Tables 5 and 9, and methods of modulating such receptors are encompassed herein.

Methods of therapy comprising administering a compound of formula (I), or a salt or solvate thereof, or a pharmaceutical composition comprising any of the foregoing, to an individual are provided. In one variation, the method comprises administering a compound of formula (MI), (MII), (MIII), (MIV) or (MV) to an individual in an amount effective to modulate a receptor, such as a receptor listed in Tables 5 and 9. In one aspect, a method of modulating the norepinephrine transporter in an individual is provided, wherein the method comprises administering a compound of the formula (MI), or a salt or solvate thereof to the individual. In another aspect, a method of modulating the progesterone receptor in an individual is provided, wherein the method comprises administering a compound of the formula (MII), or a salt or solvate thereof to the individual. In another aspect, a method of modulating the sigma receptor in an individual is provided, wherein the method comprises administering a compound of the formula (MIV), or a salt or solvate thereof to the individual.

In some embodiments, a compound as described herein that modulates a receptor (a receptor modulator) inhibits binding of a ligand by at least about or about any one of 10%, 20%, 30%, 40%, 50%, 60%, 70%, 80%, 90%, 95% or 100% as determined in the assays described herein. In some embodiments, the receptor modulator reduces an activity of a receptor by at least about or about any of 10%, 20%, 30%, 40%, 50%, 60%, 70%, 80%, 90%, 95% or 100% as compared to the corresponding activity in the same subject prior to treatment with the receptor modulator or compared to the corresponding activity in other subjects not receiving the receptor modulator. In some embodiments, the receptor modulator enhances an activity of a receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the receptor modulator or compared to the corresponding activity in other subjects not receiving the receptor modulator. In some embodiments, the receptor modulator is capable of binding to the active site of a receptor (e.g., a binding site for a ligand). In some embodiments, the receptor modulator is capable of binding to an allosteric site of a receptor.

In another aspect of the invention, provided herein is a method for preventing or treating a disease or condition disclosed herein in an individual which comprises administering to the individual an effective amount of a compound according to formulae (MI), (MII), (MIII), (MIV) or (MV), or a salt thereof, or a pharmaceutical composition comprising any of the foregoing.

In another aspect of the invention, provided herein is a method for treating prostate cancer comprising administering to an individual in need thereof a therapeutically effective amount of a compound according to formulae (MI), (MII), (MIII), (MIV) or (MV), or a salt thereof, or a pharmaceutical composition comprising any of the foregoing. In one particular embodiment with respect to the method for treating prostate cancer in an individual, the compound is according to formulae (MI) or (MII), or a salt or solvate thereof. In one particular embodiment with respect to the method for treating prostate cancer in an individual, the compound is according to formulae (MIII), (MIV) or (MV), or a salt or solvate thereof. In one particular embodiment with respect to the method for treating prostate cancer in an individual, the compound is according to formulae (MII), (MIII), or (MIV), or a salt or solvate thereof.

In one embodiment, with respect to the method of treatment, the disease or condition is selected from Parkinson's disease and Alzheimer's disease. Thus, in one embodiment, a method of treating Parkinson's disease is provided, wherein the method comprises administering to an individual a therapeutically effective amount of a compound of the formula (I), or a salt or solvate thereof. In another embodiment, a method of treating Alzheimer's disease is provided, wherein the method comprises administering to an individual a therapeutically effective amount of a compound of the formula (I), or a salt or solvate thereof.

In a particular embodiment, a method of treating Parkinson's disease is provided, wherein the method comprises administering to an individual in need thereof a compound of the formula (MI), or a salt or solvate thereof, or pharmaceutical composition comprising any of the foregoing. In another embodiment, a method of treating Alzheimer's disease is provided wherein the method comprises administering to an individual in need thereof a compound of the formula (MI), or a salt or solvate thereof, or pharmaceutical composition comprising any of the foregoing.

Methods of treating prostate cancer, alopecia, hepatocellular carcinoma, or acne vulgaris are also provided, wherein the method comprises administering to an individual a therapeutically effective amount of a compound of the formula (I), or a salt or solvate thereof. In one aspect, the method comprises administering a compound of the formula (MI), (MII), (MIII) or (MIV). In one embodiment, the method is a method of treating prostate cancer. In another embodiment, the method is a method of treating alopecia. In yet another embodiment, the method is a method of treating hepatocellular carcinoma. In still another embodiment, the method is a method of treating acne vulgaris.

In a particular variation, a method of treating prostate cancer, alopecia, hepatocellular carcinoma, or acne vulgaris are provided, wherein the method comprises administering to an individual a compound of the formula (MI), or a salt or solvate thereof. In another variation, a method of treating prostate cancer, alopecia, hepatocellular carcinoma, or acne vulgaris are is provided, wherein the method comprises administering to an individual a compound of the formula (MII), or a salt or solvate thereof. In a further embodiment, a method of treating prostate cancer, alopecia, hepatocellular carcinoma, or acne vulgaris is provided, wherein the method comprises administering to an individual a compound of the formula (MIII), or a salt or solvate thereof. In another embodiment, a method of treating prostate cancer, alopecia, hepatocellular carcinoma, or acne vulgaris is provided, wherein the method comprises administering to an individual a compound of the formula (MIV), or a salt or solvate thereof.

In another variation, a birth control method for a female individual is provided, wherein the method comprises administering a compound of the formula (MII) to the individual. In one variation, the compound is administered to the individual in an amount to prevent pregnancy. In another variation, the compound is administered to the individual in an amount to abort pregnancy. In one variation, compound (MII) is given to a female individual who is pregnant. In another variation, compound (MII) is given to a female individual who is not pregnant.

In a further variation, a method of treating depression is provided, wherein the method comprises administering to an individual a therapeutically effective amount of a compound of the formula (MIV), or a salt or solvate thereof, or a pharmaceutical composition comprising any of the foregoing.

In a further variation, a method of treating an attention deficit disorder is provided, wherein the method comprises administering to an individual a therapeutically effective amount of a compound of the formula (MI), or a salt or solvate thereof, or a pharmaceutical composition comprising any of the foregoing.

In any of the methods provided, in one aspect the individual is a human.

In one embodiment, treatment of a disease or condition with a compound of the invention or a pharmaceutically acceptable salt thereof is accompanied by no or fewer side effects than are associated with currently available therapies for the disease or condition and/or improves the quality of life of the individual.

A treatment regimen involving a compound of the formula (I) may involve administering the compound to an individual, such as a human, in dose of between about 0.01 and about 10 mg/kg of body weight, at least once a day and during the period of time required to achieve the therapeutic effect. In other variations, the daily dose (or other dosage frequency) of a compound of the formula (I) is between about 0.01 and about 8 mg/kg; or between about 0.01 to about 6 mg/kg; or between about 0.01 and about 4 mg/kg; or between about 0.01 and about 2 mg/kg; or between about 0.01 and about 1 mg/kg; or between about 0.03 and about 10 mg/kg; or between about 1 and about 10 mg/kg; or between about 2 and about 10 mg/kg; or between about 4 to about 10 mg/kg; or between about 6 to about 10 mg/kg; or between about 8 to about 10 mg/kg; or between about 0.1 and about 5 mg/kg; or between about 0.1 and about 4 mg/kg; or between about 0.5 and about 5 mg/kg; or between about 1 and about 5 mg/kg; or between about 1 and about 4 mg/kg; or between about 2 and about 4 mg/kg; or between about 1 and about 3 mg/kg; or between about 1.5 and about 3 mg/kg; or between about 2 and about 3 mg/kg; or between about 0.03 and 4 mg/kg; or between about 0.03 mg/kg and 2 mg/kg; or between about 0.05 and 10 mg/kg; or between about 0.05 and 8 mg/kg; or between about 0.05 and 4 mg/kg; or between about 0.05 and about 3 mg/kg; or between about 10 kg to about 50 kg; or between about 10 to about 100 mg/kg or between about 10 to about 250 mg/kg; or between about 50 to about 100 mg/kg or between about 50 and 200 mg/kg; or between about 100 and about 200 mg/kg or between about 200 and about 500 mg/kg; or a dosage over about 100 mg/kg; or a dosage over about 500 mg/kg.

A compound of the formula (I) may be administered to an individual in accordance with an effective dosing regimen for a desired period of time or duration, such as at least about one week, at least about 2 weeks, at least about three weeks, at least about one month, at least about 2 months, at least about 3 months, at least about 6 months, or at least about 12 months or longer. In one variation, a compound of the formula (I) is administered to an individual on a daily or intermittent schedule for the duration of the individual's life.

The dosing frequency of a compound of the formula (I) can be about a once weekly dosing. The dosing frequency of a compound of the formula (I) can be about a once daily dosing, twice daily dosing, or three times daily dosing. The dosing frequency of a compound of the formula (I) can be about three times a week dosing or about a four times a week dosing or can be about a two times a week dosing. The dosing frequency of a compound of the formula (I) can be more than about once weekly dosing but less than about daily dosing. The dosing frequency of a compound of the formula (I) can be about a once monthly dosing. The dosing frequency of a compound of the formula (I) can be about a twice weekly dosing. The dosing frequency of a compound of the formula (I) can be more than about once monthly dosing but less than about once weekly dosing. The dosing frequency of a compound of the formula (I) can be intermittent (e.g., once daily dosing for 7 days followed by no doses for 7 days, repeated for any 14 day time period, such as about 2 months, about 4 months, about 6 months or more). The dosing frequency of a compound of the formula (I) can be continuous (e.g., once weekly dosing for continuous weeks). Any of the dosing frequencies can employ any of the compounds described herein, or a salt or solvate thereof, together with any of the dosages described herein.

Kits

The invention further provides kits comprising a compound of formula (I). The kits may optionally include a set of instructions, generally written instructions, although electronic storage media (e.g., magnetic diskette or optical disk) containing instructions are also acceptable. The instructions included with the kit generally include information as to the components and their administration to an individual, such as information regarding dosage, dosing schedule, and route of administration. In some embodiments, the kit includes (a) a compound of formula (I) or a pharmaceutically acceptable salt thereof; and (b) instructions for use in a condition or disorder described herein, such as prostate cancer, Alzheimer's disease and Parkinson's disease. The kits may be used for any one or more of the uses described herein, and, accordingly, may contain instructions for any one or more of the stated uses (e.g., treating and/or preventing and/or delaying the onset and/or the development of any indication disclosed herein).

In some embodiments, the amount of compound of the formula (I) in a kit is an amount sufficient to produce a desired therapeutic outcome (e.g., reducing the severity or duration of, stabilizing the severity of, or eliminating one or more symptoms of an indication to be treated).

Kits generally comprise suitable packaging. The kits may comprise one or more containers comprising any compound(s) described herein. Suitable packaging includes, but is not limited to, vials, bottles, jars, flexible packaging (e.g., plastic bags), and the like. Each component (where there is more than one component) can be packaged in separate containers or some components can be combined in one container where cross-reactivity and shelf life permit. Kits may optionally provide additional components such as excipients.

The containers may be unit dosage forms, bulk packages (e.g., multi-dose packages), or sub-unit doses. For example, kits may be provided that contain sufficient dosages of a compound of formula (I) to provide effective treatment of an individual having an indication to be treated for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

Methods of Preparing and Isolating Compounds of the Invention

Synthetic methods to generate diarylhydantoin compounds are described in U.S. Publication Nos. 2007/0004753, 2007/0254933 and 2009/0111864, which are incorporated herein by reference in their entireties and specifically regarding synthetic methods. Compounds (MI)-(MV) may also be made according to the methods detailed in the Examples herein.

The following Examples are provided to illustrate but not limit the invention.

Example 1

Isolation and Identification of Compounds from Rat Plasma

Metabolites of RD162' were isolated and identified in steady-state plasma samples from the high-dose group of a 26-week oral toxicology study in male and female Sprague Dawley rats.

Rat plasma samples were stored at approximately −20° C. or colder. Samples were obtained from subjects receiving RD162'. The study samples were prepared for HPLC injection by precipitating each sample (100 µL) with a 3-x volume (300 µL) of acetonitrile. The samples were centrifuged at 16,000 g for 5 min. Following centrifugation, 380 µL of each supernatant was transferred to a new tube and evaporated to dryness in a Speed-Vac. The evaporated samples were reconstituted in 50 µL of 0.2% formic acid in water.

Samples were analyzed using the following LC/MS/MS conditions: HPLC: Shimadzu VP System; Mobile Phase: 0.2% formic acid in water (A) and 0.15% formic acid in methanol (B); Column: 1×50 mm TITAN C18 column (Peeke Scientific); Injection Volume: 20 µL; Gradient: 5-75% B in 30 min; Flow Rate: 100 µL/min; Mass Spectrometer: Applied Biosystems/MDS SCIEX Q-STAR; Interface: IonSpray split at ~$\frac{1}{10}$; Parent Ion Scan: TOF Positive from 100-900 amu; Product Ion Scan: TOF Product Ion from 60-900 amu of most intense ion in Parent Ion Scan; TOF Calibration: Externally calibrated using Renin Substrate.

The samples were prepared for injection and analyzed the same day. Table 1 summarizes the results of this analysis.

TABLE 1

Summary of RD162' Metabolites Identified by LC/MS/MS in Rat Plasma Samples

| Name | RT (min) | Compound or Metabolite (m/z) | MS Peak Area Animal No. (TK Sample Time) | | |
|---|---|---|---|---|---|
| | | | 1591 (2 h) | 1590 (8 h) | 1709 (8 h) |
| RD 162' | 26.0 | 465 | $5.9\ e^5$ | $4.0\ e^5$ | $1.1\ e^6$ |
| (MI) | 27.8 | 452 | $1.3\ e^4$ | $1.0\ e^4$ | $1.8\ e^4$ |
| (MII) | 25.1 | 451 | $7.5\ e^3$ | $4.2\ e^3$ | $1.2\ e^4$ |
| (MIII) | 23.3 | 435 | ND | ND | ND |
| (MIV) | 24.1 | 449 | $6.1\ e^4$ | $3.2\ e^4$ | $3.0\ e^4$ |

Example 2

Isolation and Identification of Compounds in Dog Plasma

Metabolites of RD162' were isolated and identified in steady-state plasma samples from the high-dose group of a 13-week oral toxicology study in male beagle dogs.

Dog plasma samples were stored at approximately −20° C. or colder. Samples were obtained from subjects receiving RD162'. The study samples were prepared for HPLC injection by precipitating each sample (100 µL) with a 3-x volume (300 µL) of acetonitrile. The samples were centrifuged at 16,000 g for 5 min. Following centrifugation, 380 µL of each supernatant was transferred to a new tube and evaporated to dryness in a Speed-Vac. The evaporated samples were reconstituted in 50 µL of 0.2% formic acid in water.

Samples were analyzed using the following LC/MS/MS conditions: HPLC: Shimadzu VP System; Mobile Phase: 0.2% formic acid in water (A) and 0.15% formic acid in methanol (B); Column: 1×50 mm TITAN C18 column (Peeke Scientific); Injection Volume: 20 µL; Gradient: 5-75% B in 30 min; Flow Rate: 100 µL/min; Mass Spectrometer: Applied Biosystems/MDS SCIEX Q-STAR; Interface: IonSpray split at ~$\frac{1}{10}$; Parent Ion Scan: TOF Positive from 100-900 amu; Product Ion Scan: TOF Product Ion from 60-900 amu of most intense ion in Parent Ion Scan; TOF Calibration: Externally calibrated using Renin Substrate.

The samples were prepared for injection and analyzed the same day. Table 2 summarizes the results of this analysis.

TABLE 2

Summary of RD162' Metabolites Identified by LC/MS/MS in Dog Plasma Samples

| | | | MS Peak Area Animal No. (TK Sample Time) | | | |
|---|---|---|---|---|---|---|
| Name | RT (min) | Compound or Metabolite (m/z) | 119 (2 h) | 119 (4 h) | 123 (2 h) | 123 (4 h) |
| RD 162' | 26.0 | 465 | $6.3\,e^5$ | $3.1\,e^5$ | $3.8\,e^5$ | $4.2\,e^5$ |
| (MI) | 27.8 | 452 | $5.6\,e^4$ | $5.6\,e^4$ | $2.5\,e^4$ | $2.4\,e^4$ |
| (MII) | 25.1 | 451 | $7.5\,e^3$ | $2.7\,e^3$ | $5.8\,e^3$ | $5.1\,e^3$ |
| (MIII) | 23.3 | 435 | ND | ND | ND | ND |
| (MIV) | 24.1 | 449 | $3.7\,e^3$ | $7.9\,e^2$ | $2.1\,e^3$ | $2.3\,e^3$ |

Example 3

Isolation and Identification of Compounds in Human Plasma

Metabolites of RD162' were isolated and identified in steady-state plasma samples from prostate cancer patients taking RD162'. The steady-state human samples consisted of five $C_{max}$ samples that were obtained on approximately Day 84 of treatment at 240 mg/day.

Human plasma samples were stored at approximately −20° C. or colder. Samples were obtained from subjects receiving RD162'. The study samples were prepared for HPLC injection by precipitating each sample (100 μL) with a 3-x volume (300 μL) of acetonitrile. The samples were centrifuged at 16,000 g for 5 min. Following centrifugation, 380 μL of each supernatant was transferred to a new tube and evaporated to dryness in a Speed-Vac. The evaporated samples were reconstituted in 50 μL of 0.2% formic acid in water.

Samples were analyzed using the following LC/MS/MS conditions: HPLC: Shimadzu VP System; Mobile Phase: 0.2% formic acid in water (A) and 0.15% formic acid in methanol (B); Column: 1×50 mm TITAN C18 column (Peeke Scientific); Injection Volume: 20 μL; Gradient: 5-75% B in 30 min; Flow Rate: 100 μL/min; Mass Spectrometer: Applied Biosystems/MDS SCIEX Q-STAR; Interface: IonSpray split at ~1/10; Parent Ion Scan: TOF Positive from 100-900 amu; Product Ion Scan: TOF Product Ion from 60-900 amu of most intense ion in Parent Ion Scan; TOF Calibration: Externally calibrated using Renin Substrate.

The samples were prepared for injection and analyzed the same day. Table 3 summarizes the results of this analysis.

TABLE 3

Summary of RD162' Metabolites Identified by LC/MS/MS in Human Plasma Samples

| | | | MS Peak Area Subject ID (PK Sample Time) | | | | |
|---|---|---|---|---|---|---|---|
| Name | RT (min) | Compound or Metabolite (m/z) | 3478 (1 h) | 1473 (1 h) | 3475 (1 h) | 1472 (1 h) | 3454 (2 h) |
| RD 162' | 26.0 | 465 | $6.4\,e^5$ | $6.3\,e^5$ | $5.0\,e^5$ | $5.4\,e^5$ | $5.7\,e^5$ |
| (MI) | 27.8 | 452 | $3.8\,e^4$ | $4.5\,e^4$ | $2.5\,e^4$ | $5.4\,e^4$ | $6.2\,e^4$ |
| (MII) | 25.1 | 451 | $1.7\,e^5$ | $1.6\,e^5$ | $1.5\,e^5$ | $1.5\,e^5$ | $1.6\,e^5$ |
| (MIII) | 23.3 | 435 | $2.2\,e^4$ | $1.3\,e^4$ | $1.9\,e^4$ | $1.6\,e^4$ | $1.6\,e^4$ |

Example 4

Quantification of Compounds in Human Plasma

To estimate the concentrations of the metabolites in human plasma, LC/MS/MS assays for (MI), (MII), and (MIII) were qualified and used to analyze plasma from 18 prostate cancer patients who had received RD162' at 150 to 480 mg per day for approximately three months. The results of this analysis (Table 4) showed that (MI) and (MII) were present at high concentrations in the plasma, and (MIII) was present at low concentrations.

TABLE 4

Concentrations of RD162' Metabolites in Plasma from Patients Treated with RD162' for at Least Three Months

| Summary Statistics for Results from | Concentrations in Patients' Plasma Expressed as a Percentage of the Concentration of RD162' | | |
|---|---|---|---|
| 18 Patients | (MI) | (MII) | (MIII) |
| Minimum | 16% | 49% | 1% |
| Maximum | 259% | 204% | 14% |
| Average | 60% | 112% | 4% |

The method used to derive the above data was as follows. Electrospray LC/MS/MS Assay of RD162' Metabolites ((MI), (MII), (MIII)):

Plasma Extraction Procedures for Concentration Determinations: A human plasma sample (50 μL) was added to a 10-mL glass tube. A 10-μL volume of IS stock solution was added to the tube, followed by addition of 1 M phosphate buffer at pH 3.0 (400 μL). The mixture was vortexed and tetrabutylmethyl ether (5 mL) was added. The tube was vortexed for 30 sec and then centrifuged at 4540 g for 10 min. The solvent was transferred to a glass tube and dried under air flow at 35-40° C. The sample was reconstituted with 100 μL of methanol:0.1% formic acid in water (7:3) vortexed for 30 sec, and sonicated for 5 min. The sample was transferred to an HPLC sample vial and centrifuged at 4540 g for 5 min. A 20-μL volume was then injected onto an LC/MS/MS system for assay.

LC/MS/MS Parameters for RD162' Metabolites ((MII and (MIII)): Positive Ion Mode Instrument Parameters—Function 1; Polarity: ES+; Data type: MRM data; Function type: MRM of 8 channels.

| Channel | Reaction | Dwell (sec) | Cone Volt | Col. Energy | Compound |
|---|---|---|---|---|---|
| 1 | 435.35 > 152.30 | 0.05 | 55.0 | 35.0 | (MIII) |
| 2 | 435.35 > 164.30 | 0.05 | 55.0 | 35.0 | (MIII) |
| 3 | 435.35 > 178.30 | 0.05 | 55.0 | 35.0 | (MIII) |
| 4 | 435.35 > 418.30 | 0.05 | 55.0 | 25.0 | (MIII) |
| 5 | 451.25 > 178.30 | 0.05 | 55.0 | 35.0 | (MII) |
| 6 | 451.25 > 195.40 | 0.05 | 55.0 | 27.0 | (MII) |
| 7 | 469.30 > 213.40 | 0.05 | 50.0 | 27.0 | D4-RD 162' internal standard |
| 8 | 469.30 > 384.40 | 0.05 | 50.0 | 27.0 | D4-RD 162' internal standard |

HP1100 LC Pump Initial Conditions: HPLC Column: ACE C18, 5 μM, 150×2.1 mm id. Solvents: A % 40.0; B % 60.0; C % 0.0; D % 0.0; Valve A set to channel 1; Valve B set to channel 1. Flow: 0.300 mL/min; Stop Time: 9.0 min; Min. Pressure: 0 bar; Max. Pressure: 300 bar; Oven Temperature Left: 30.0° C.; Oven Temperature Right: 30.0° C.

HP1100 LC Pump Gradient Timetable:

| Time | A % | B % | C % | D % | Flow (mL/min) | Pressure |
|---|---|---|---|---|---|---|
| 0.00 | 40.0 | 60.0 | 0.0 | 0.0 | 0.300 | 300 |
| 1.50 | 40.0 | 60.0 | 0.0 | 0.0 | 0.300 | 300 |
| 1.60 | 10.0 | 90.0 | 0.0 | 0.0 | 0.300 | 300 |
| 3.50 | 10.0 | 90.0 | 0.0 | 0.0 | 0.300 | 300 |
| 3.60 | 40.0 | 60.0 | 0.0 | 0.0 | 0.300 | 300 |

LC/MS/MS Parameters for RD162' Metabolite (MI)

Instrument Parameters—Function 1: Polarity ES−; Data type: MRM data; Function type: MRM of 5 channels.

| Channel | Reaction | Dwell (sec) | Cone Volt | Col. Energy | Compound |
|---|---|---|---|---|---|
| 1 | 373.30 > 315.20 | 0.05 | 50.0 | 35.0 | Phenylcoumarin IS |
| 2 | 373.30 > 343.30 | 0.05 | 50.0 | 25.0 | Phenylcoumarin IS |
| 3 | 373.30 > 358.30 | 0.05 | 50.0 | 25.0 | Phenylcoumarin IS |
| 4 | 450.20 > 158.00 | 0.05 | 30.0 | 30.0 | (MI) |
| 5 | 450.20 > 406.30 | 0.05 | 30.0 | 15.0 | (MI) |

HPLC Column: ACE C18, 5 μM, 150×2.1 mm id; HP1100 LC Pump mode: Isocratic; Isocratic solvent conditions: A % 25.0; B % 75.0; C % 0.0; D % 0.0; Valve A set to channel 1; Valve B set to channel 1; Flow: 0.300 mL/min; Stop Time: 4.5 min; Min. Pressure: 0 bar; Max. Pressure: 300 bar; Oven Temperature Left: 30.0° C.; Oven Temperature Right: 30.0° C.

Synthesis of Compounds of the Invention

Example 5

Preparation of 4-(3-(4-cyano-3-(trifluoromethyl) phenyl)-5,5-dimethyl-4-oxo-2-thioxoimidazolidin-1-yl)-2-fluorobenzoic acid (Compound (MI))

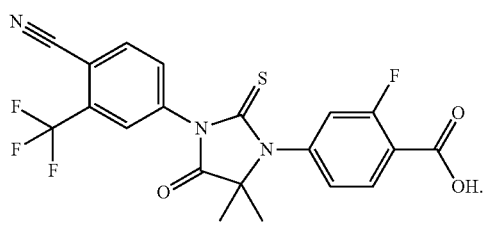 [SMILES: CC1(C)C(=O)N(c2ccc(C#N)c(C(F)(F)F)c2)C(=S)N1c1ccc(C(=O)O)c(F)c1]

4-(3-(4-Cyano-3-(trifluoromethyl)phenyl)-5,5-dimethyl-4-oxo-2-thioxoimidazolidin-1-yl)-2-fluoro-N-methylbenzamide was suspended in concentrated HCl and heated at 120° C. in a pressure vessel for 48 h. The reaction was monitored by thin layer chromatography (TLC). The reaction mixture was cooled to ambient temperature. The residue was filtered and purified by silica gel chromatography (100-200 mesh, eluent: 0-5% methanol-dichloromethane). MS (m/z): 452 (M+1). HPLC: Column, YMC ODS AQ, 4.6×250 mm, 5 μm, Mobile Phase A: 10 mM Ammonium acetate, Mobile Phase B: Acetonitrile, Gradient, Isocratic: 55% A:45% B, Retention time, 3.804 min, HPLC Purity, 95.82%, Flow Rate, 1 mL/min. $^1$H NMR (CDCl$_3$, Freebase): δ (ppm) 8.22 (t, 1H), 8.0 (d, 1H), 7.98 (s, 1H), 7.82 (d, 1H), 7.2 (m, 2H) 1.6 (s, 6H).

Example 6

Preparation of 4-(3-(4-Cyano-3-(trifluoromethyl) phenyl)-5,5-dimethyl-4-oxo-2-thioxoimidazolidin-1-yl)-2-fluorobenzamide (Compound (MII))

Example 6a

Preparation of 4-bromo-2-fluorobenzamide

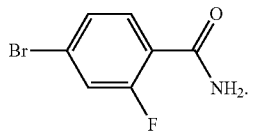 [SMILES: NC(=O)c1ccc(Br)cc1F]

To a stirred solution of 4-bromo-2-fluorobenzoic acid (1.5 g, 6.84 mmol) in DCM (15 mL) was added dropwise oxalyl chloride (3.45 g, 27.39 mmol) at 0° C. After addition was complete, 2-3 drops of DMF were added at 0° C. and the reaction mixture was stirred for 2 h at room temperature. The reaction mixture was concentrated under reduced pressure and the residue was dissolved in dry THF (20 mL). To this solution was added aq. ammonia (50 mL) at 0° C. The reaction mixture was warmed to and stirred at room temperature for 30 min. The solvent was removed under reduced pressure and the residue was azeotroped with toluene to obtain 1.3 g of product. $^1$H NMR (CDCl$_3$, Freebase): δ (ppm) 8.0 (t, 1H), 7.40 (d, 1H), 7.30 (d, 1H), 6.60 (bs, 1H), 5.9 (bs, 1H).

Example 6b

Preparation of 2-(4-carbamoyl-3-fluorophenylamino)-2-methylpropanoic acid

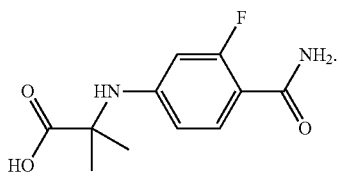 [SMILES: CC(C)(Nc1ccc(C(N)=O)c(F)c1)C(=O)O]

4-Bromo-2-fluorobenzamide (0.5 g, 2.29 mmol), 2 aminoisobutyric acid (0.354 g, 3.54 mmol), CuI (87 mg, 0.458 mmol), and K$_2$CO$_3$ (0.790 g, 5.72 mmol) were mixed in DMF (5 mL). H$_2$O (0.5 mL) and TEA (11 mg, 0.1 mmol) were added followed by 2-acetyl cyclohexanone (60 mg, 0.428 mmol). The reaction mixture was heated to 95-100° C. for 48 h. The reaction mixture was diluted with H$_2$O (20 mL) and the aqueous layer was washed with ethyl acetate (20 mL). The aqueous layer was acidified with 1M citric acid to pH 4 and the product was extracted with ethyl acetate (20 mL×3). The combined organic layer was dried over anhydrous Na$_2$SO$_4$ and concentrated under reduced pressure to obtain the product. $^1$H NMR (DMSO, Freebase): δ (ppm) 7.55-7.45 (t, 1H), 7.20 (bs, 1H), 7.05 (bs, 1H), 6.80 (bs, 1H), 6.35-6.30 (d, 1H), 6.18-6.10 (d, 1H), 1.42 (s, 6H).

Example 6c

Preparation of methyl 2-(4-carbamoyl-3-fluorophenylamino)-2-methylpropanoate

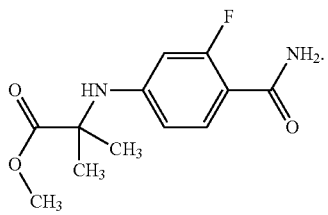 [SMILES: COC(=O)C(C)(C)Nc1ccc(C(N)=O)c(F)c1]

A solution of 2-(4-carbamoyl-3-fluorophenylamino)-2-methylpropanoic acid and $K_2CO_3$ (1.5 equivalents) in DMF (10 fold) was stirred at RT for 10 min. MeI (1.5 equivalents) was added and the reaction mixture was heated at 55-60° C. for 2 h. The solvent was removed under reduced pressure and the reaction mixture was poured in water, extracted with ethyl acetate (100 mL×2), dried over $Na_2SO_4$, concentrated and purified by column chromatography. $^1H$ NMR ($CDCl_3$, Freebase): δ (ppm) 7.9 (t, 1H), 6.5 (bs, 1H), 6.4 (d, 1H), 6.2 (d, 1H), 5.6 (bs, 1H), 4.6 (bs, 1H), 3.75 (s, 3H), 1.6 (s, 6H).

Example 6d

Preparation of 4-isothiocyanato-2-(trifluoromethyl)benzonitrile

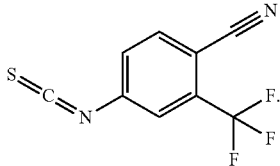 [SMILES: N#Cc1ccc(N=C=S)cc1C(F)(F)F]

Thiophosgene (10 g, 87.71 mmol) was dissolved in water and stirred at room temperature for 10 min. 4-Amino-2-trifluoromethyl-benzonitrile was added portionwise at room temperature. The reaction mixture was stirred at room temperature for 2 h. The product was extracted with dichloromethane, and the organic layer was washed with water, brine, dried over sodium sulfate and evaporated to obtain 12 g of product. $^1H$ NMR ($CDCl_3$): δ (ppm) 7.84 (d, 1H), 7.58 (s, 1H), 7.48 (d, 1H).

Example 6e

Preparation of 4-(3-(4-cyano-3-(trifluoromethyl)phenyl)-5,5-dimethyl-4-oxo-2-thioxoimidazolidin-1-yl)-2-fluorobenzamide (Compound (MII))

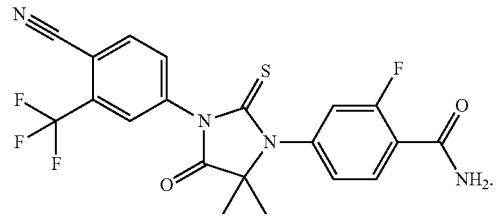 [SMILES: CC1(C)C(=O)N(c2ccc(C#N)c(C(F)(F)F)c2)C(=S)N1c1ccc(C(N)=O)c(F)c1]

A solution of methyl 2-(4-carbamoyl-3-fluorophenylamino)-2-methylpropanoate and 2-(trifluoromethyl)-4-isothiocyanatobenzonitrile (1.5 equivalents) in dry DMSO (5 mL per mmol) was heated to 80-82° C. for 12 h. The reaction mixture was diluted with water and extracted with ethyl acetate. The combined organic layer was concentrated under reduced pressure and the residue was purified by silica gel chromatography eluting with 40% Acetone-Hexanes. MS (m/z): 451 (M+1). HPLC: Column, YMC ODS A, 4.6×150 mm, 5 μm, Mobile Phase A: 10 mM Ammonium acetate, Mobile Phase B: Acetonitrile, Gradient, 10% B up to 2 min, 10% to 90% B in 3 min, hold for 3 min, 90% to 10% B in 5 min, Retention time, 2.782 min, HPLC Purity, 99.4%, Flow Rate, 1 mL/min. $^1H$ NMR ($CDCl_3$, Freebase): δ (ppm) 8.3 (t, 1H), 8.0 (d, 1H) 7.98 (s, 1H), 7.8 (d, 1H), 7.27 (d, 1H), 7.2 (d, 1H), 6.65 (d, 1H), 6.0 (s, 1H), 1.62 (s, 6H).

Example 7

Preparation of 4-(3-(4-cyano-3-(trifluoromethyl)phenyl)-5,5-dimethyl-2,4-dioxoimidazolidin-1-yl)-2-fluorobenzamide (Compound (MIII))

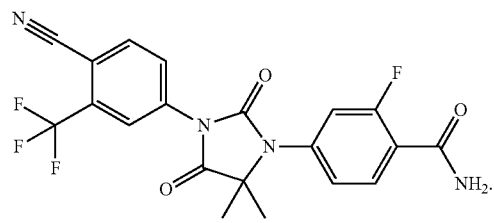 [SMILES: CC1(C)C(=O)N(c2ccc(C#N)c(C(F)(F)F)c2)C(=O)N1c1ccc(C(N)=O)c(F)c1]

To a solution of 4-(3-(4-cyano-3-(trifluoromethyl)phenyl)-5,5-dimethyl-4-oxo-2-thioxoimidazolidin-1-yl)-2-fluorobenzamide (Compound (MII)) (1.48 g, 3.4 mmol) in ethanol (60 mL) was added 30% aqueous $H_2O_2$ (30 mL) at room temperature. The solution was heated to reflux for 1 h. After removal of ethanol, brine (100 mL) was added and the aqueous layer was extracted with ethyl acetate. The organic layer was dried over sodium sulfate and concentrated under reduced pressure to obtain the crude product that was purified by silica gel chromatography. MS (m/z): 435 (M+1). HPLC: Column, YMC ODS A, 4.6×150 mm, 5 μm, Mobile Phase A: 10 mM Ammonium acetate, Mobile Phase B: Acetonitrile, Gradient, 10% B up to 2 min, 10% to 90% B in 6 min, hold for 10 min, 90% to 10% B in 4 min, Retention time, 9.548 min, HPLC Purity, 98.08%, Flow Rate, 1 mL/min. $^1H$ NMR ($CDCl_3$, Freebase): δ (ppm) 8.3 (t, 1H), 8.18 (s, 1H), 8.2 (d, 1H), 7.96 (d, 1H), 7.25 (m, 2H), 6.65 (bd, 1H), 5.9 (bs, 1H) 1.65 (s, 6H).

Example 8

Preparation of 4-(3-(4-cyano-3-(trifluoromethyl)phenyl)-5,5-dimethyl-2,4-dioxoimidazolidin-1-yl)-2-fluoro-N-methylbenzamide (Compound (MIV))

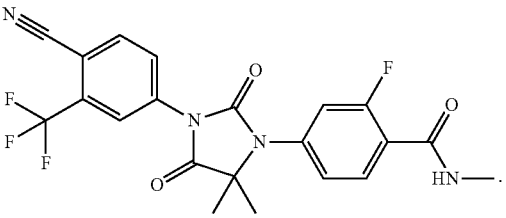 [SMILES: CNC(=O)c1ccc(N2C(=O)N(c3ccc(C#N)c(C(F)(F)F)c3)C(=O)C2(C)C)cc1F]

To a solution of 4-(3-(4-cyano-3-(trifluoromethyl)phenyl)-5,5-dimethyl-4-oxo-2-thioxoimidazolidin-1-yl)-2-fluoro-N-methylbenzamide (1.52 g, 3.4 mmol) in ethanol (60 mL) was added 30% aqueous $H_2O_2$ (30 mL) at room temperature. The solution was heated to reflux for 1 h. After removal of ethanol, brine (100 mL) was added and the aqueous layer was extracted with ethyl acetate. The organic layer was dried over sodium sulfate and concentrated under reduced pressure to obtain the crude product that was purified by silica gel chromatography. MS (m/z), 449 (M+1). HPLC: Column, YMC ODS A, 4.6×150 mm, 5 μm, Mobile Phase A: 10 mM Ammonium acetate, Mobile Phase B: Acetonitrile, Gradient, 10% B up to 2 min, 10% to 90% B in 3 min, hold for 3 min, 90% to 10% B in 5 min, Retention time, 8.976 min, HPLC Purity, 98.46%, Flow Rate, 1 mL/min. $^1$H NMR (CDCl$_3$, Freebase): δ (ppm) 8.22 (t, 1H), 8.18 (s, 1H), 8.04 (d, 1H), 7.95 (d, 1H), 7.28 (d, 1H), 7.22 (d, 1H), 6.70 (m, 1H), 3.05 (d, 3H), 1.65 (s, 6H).

Example 9

Preparation of 4-(3-(4-cyano-3-(trifluoromethyl)phenyl)-5,5-dimethyl-2,4-dioxoimidazolidin-1-yl)-2-fluorobenzoic acid (Compound (MV))

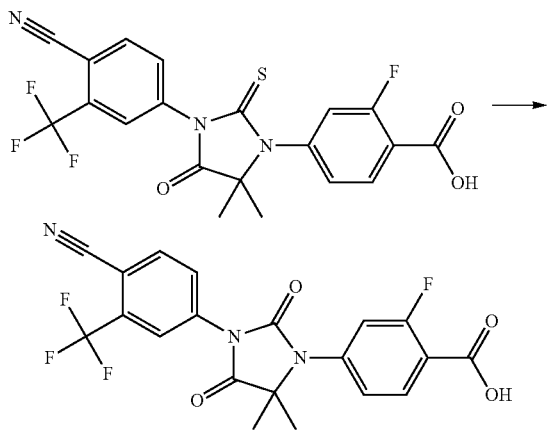

A solution of 4-(3-(4-cyano-3-(trifluoromethyl)phenyl)-5,5-dimethyl-4-oxo-2-thioxoimidazolidin-1-yl)-2-fluorobenzoic acid (50 mg, 0.11 mmol) in thionyl chloride (0.5 mL, 67.7 mmol) was stirred at 90 deg C. for 15 h. The reaction mixture was concentrated under reduced pressure to dryness. Ice-water (20 mL) was added into the residue and the product was extracted with ethyl acetate (60 mL). The organic layer was dried over anhydrous sodium sulfate and evaporated under reduced pressure to afford crude product, which was purified by reverse phase HPLC to yield 4-(3-(4-cyano-3-(trifluoromethyl)phenyl)-5,5-dimethyl-2,4-dioxoimidazolidin-1-yl)-2-fluorobenzoic acid. $^1$H NMR DMSO-d6 (FREE BASE): δ (ppm) 8.39 (d, 1H), 8.25 (s, 1H), 8.1 (d, 1H), 8.0 (t, 1H), 7.45 (d, 1H), 7.4 (d, 1H), 1.58 (s, 6H).

Biological Activity of Test Compounds

The following examples illustrate the biological activity of Compounds (MI)-(MIV). Standard binding and enzyme assays such as those described below can be performed by practitioners such as, for example, Cerep, Inc. (Redmond, Wash., USA); MDS Pharma Services (King of Prussia, Pa. USA); NovaScreen Biosciences/Caliper Life Sciences (Mountain View, Calif., USA); and EuroScreen FAST (Gosselies, Belgium).

DEFINITIONS

The following receptor abbreviations are used in the following examples: Adenosine for $A_1$, $A_{2a}$ and $A_3$; Adrenergic for $\alpha_1$ and $\alpha_2$; Angiotensin for $AT_1$ and $AT_2$; Benzodiazepine for BZD; Bradykinin for $B_1$ and $B_2$; Cannabinoid for $CB_1$ and $CB_2$; Cholecystokinin for $CCK_1$ and $CCK_2$; Corticotropin Releasing Factor for $CRF_1$; Dopamine for $D_1$, $D_{2S}$, $D_3$, $D_{4.4}$; Endothelin for $ET_A$ and $ET_B$; Gamma-aminobutyric acid for GABA; Ionotropic gamma-aminobutyric acid for $GABA_A$; Alpha-amino-3-hydroxyl-5-methyl-4-isoxazolepropionate for AMPA; N-Methyl-D-aspartic acid for NMDA; Histamine for $H_1$, $H_2$ and $H_3$; Leukotriene for $LTB_4$ and $LTD_4$; Gonadotropin Releasing Hormone for GnRH; Melanocortin for $MC_4$; Muscarinic for M; Neurokinin for $NK_1$, $NK_2$ and $NK_3$; Neuropeptide for Y; Nociceptin opioid for NOP; Phencyclidine for PCP; Purinergic for P2X and P2Y; Serotonin for 5-HT; Somatostatin for $sst_5$; Glucocorticoid for GR; Estrogen for ER; Progesterone for PR; Thyroid hormone for TR; Thyrotropin Releasing Hormone for $TRH_1$; Vasopressin for $V_{1a}$ and $V_2$; ATP-Sensitive $K^+$ for $K_{ATP}$; Voltage-gated $K^+$ for $K_V$; and Small-conductance $Ca^{2+}$-dependent for $SK_{Ca}$. The following enzyme abbreviations are used in the following examples: Phosphodiesterase for PDE1B, PDE2A, PDE3A, PDE4D, PDE5; Protein Kinase C alpha for PKCα; Catechol-O-methyl transferase for COMT; Monoamine oxidase for MAO-A and MAO-B; and Phenylethanolamine-N-methyl transferase for PNMT.

Example B1

In-Vitro Pharmacology: Binding Activity of Compounds (MI)-(MIV)

Compounds (MI)-(MIV) were evaluated by screening at 10 μM against the targets shown in Table 5. Radioligand binding assay methods utilized to measure the activity of compounds of the invention will be familiar to those skilled in the art. For each binding assay, the general procedures and experimental conditions are summarized in Tables 5 and 6, respectively. In each assay case, the assay components such as, for example, the cell-type, ligand, reference compound and the like, will be familiar to practitioners of such an assay.

TABLE 5

| Assay | Origin | Reference Compound |
|---|---|---|
| General Procedures | | |
| $A_1$ (h) (aa) | $hr^1$(CHO cells) | DPCPX |
| $A_{2A}$ (h) (ag) | $hr^1$ (HEK-293 cells) | NECA |
| $A_3$ (h) (ag) | $hr^1$ (HEK-293 cells) | IB-MECA |
| $\alpha_1$ (ns)$^2$ (aa) | rat cerebral cortex | prazosin |
| $\alpha_2$ (ns)$^2$ (aa) | rat cerebral cortex | yohimbine |

TABLE 5-continued

| General Procedures | | |
|---|---|---|
| Assay | Origin | Reference Compound |
| $\beta_1$ (h) (ag) | hr[1] (HEK-293 cells) | atenolol |
| $\beta_2$ (h) (ag) | hr[1] (CHO cells) | ICI 118551 |
| $AT_1$ (h) (aa) | hr[1] (HEK-293 cells) | saralasin |
| $AT_2$ (h) (ag) | hr[1] (CHO cells) | saralasin |
| BZD (central) (ag) | rat cerebral cortex | diazepam |
| $B_1$ (h) (ag) | hr[1] (CHO cells) | desArg[10]-KD |
| $B_2$ (h) (ag) | hr[1] (CHO cells) | NPC 567 |
| $CB_1$ (h) (ag) | hr[1] (CHO cells) | CP 55940 |
| $CB_2$ (h) (ag) | hr[1] (CHO cells) | WIN 55212-2 |
| $CCK_1$ ($CCK_A$) (h) (ag) | hr[1] (CHO cells) | CCK-8s |
| $CCK_2$ ($CCK_B$) (h) (ag) | hr[1] (CHO cells) | CCK-8s |
| $CRF_1$ (h) (ag) | hr[1] (CHO cells) | sauvagine |
| $D_1$ (h) (aa) | hr[1] (CHO cells) | SCH 23390 |
| $D_{2S}$ (h) (aa) | hr[1] (HEK-293 cells) | (+)butaclamol |
| $D_3$ (h) (aa) | hr[1] (CHO cells) | (+)butaclamol |
| $D_{4.4}$ (h) (aa) | hr[1] (CHO cells) | Clozapine |
| $ET_A$ (h) (ag) | hr[1] (CHO cells) | endothelin-1 |
| $ET_B$ (h) (ag) | hr[1] (CHO cells) | endothelin-3 |
| GABA (ns)[2] (ag) | rat cerebral cortex | GABA |
| AMPA (ag) | rat cerebral cortex | L-glutamate |
| kainate (ag) | rat cerebral cortex | kainic acid |
| NMDA (aa) | rat cerebral cortex | CGS 19755 |
| $H_1$ (h) (aa) | hr[1] (HEK-293 cells) | pyrilamine |
| $H_2$ (h) (aa) | hr[1] (CHO cells) | cimetidine |
| $H_3$ (h) (ag) | hr[1] (CHO cells) | (R)α-Me-histamine |
| $I_2$ (aa) | rat cerebral cortex | idazoxan |
| $BLT_1$ ($LTB_4$) (h) (ag) | hr[1] (CHO cells) | $LTB_4$ |
| $CysLT_1$ ($LTD_4$) (h) (ag) | hr[1] (CHO cells) | $LTD_4$ |
| GnRH (LH-RH) (ag) | rat pituitary gland | [D-Trp[6]]-LH-RH |
| $MC_4$ (h) (ag) | hr[1] (CHO cells) | NDP-α-MSH |
| M (ns)[2] (aa) | rat cerebral cortex | Atropine |
| $NK_1$ (h) (ag) | U-373MG cells (endogenous) | [Sar[9],Met($O_2$)[11]]-SP |
| $NK_2$ (h) (ag) | hr[1] (CHO cells) | [Nleu[10]]-NKA (4-10) |
| $NK_3$ (h) (aa) | hr[1] (CHO cells) | SB 222200 |
| Y (ns)[2] (ag) | rat cerebral cortex | NPY |
| N neuronal α-BGTX-insensitive (α4β2) (ag) | rat cerebral cortex | nicotine |
| opioid (ns)[2] (aa) | rat cerebral cortex | naloxone |
| NOP (ORL1) (h) (ag) | hr[1] (HEK-293 cells) | nociceptin |
| PCP (aa) | rat cerebral cortex | MK 801 |
| P2X (ag) | rat urinary bladder | α β-MeATP |
| P2Y (ag) | rat cerebral cortex | dATPαS |
| 5-HT (ns)[2] (ag) | rat cerebral cortex | serotonin |
| σ (ns)[2] (ag) | rat cerebral cortex | haloperidol |
| $sst_5$ (h) (ag) | hr[1] (CHO cells) | somatostatin-14 |
| GR (h) (ag) | IM-9 cells (cytosol) | dexamethasone |
| ER (ns)[2] (h) (ag) | MCF-7 cells (cytosol) | 17-β-estradiol |
| PR (h) (ag) | T47D cells (cytosol) | promegestone |
| TR (TH) (ag) | rat liver | $T_3$ |
| $TRH_1$ (h) (ag) | hr[1] (CHO cells) | TRH |
| $V_{1a}$ (h) (ag) | hr[1] (CHO cells) | [d($CH_2$)$_5$[1],Tyr(Me)$_2$]-AVP |
| $V_2$ (h) (ag) | hr[1] (CHO cells) | AVP |
| $Ca^{2+}$ channel (L, dihydropyridine site) (aa) | rat cerebral cortex | nitrendipine |
| $Ca^{2+}$ channel (L, diltiazem site) (benzothiazepines) (aa) | rat cerebral cortex | diltiazem |
| $Ca^{2+}$ channel (L, verapamil site) (phenylalkylamine) (aa) | rat cerebral cortex | D 600 |
| $K_{ATP}$ channel (aa) | rat cerebral cortex | glibenclamide |
| hERG (membrane preparation) (aa) | hr[1] (HEK-293 cells) | astemizole |
| $K_V$ channel (aa) | rat cerebral cortex | α-dendrotoxin |
| $SK_{Ca}$ channel (aa) | rat cerebral cortex | apamin |
| $Na^+$ channel (site 2) (aa) | rat cerebral cortex | veratridine |
| $Cl^-$ channel (GABA-gated) (aa) | rat cerebral cortex | picrotoxinin |
| norepinephrine transporter (h) (aa) | hr[1] (CHO cells) | protriptyline |
| dopamine transporter (h) (aa) | hr[1] (CHO cells) | BTCP |
| GABA transporter (aa) | rat cerebral cortex | nipecotic acid |
| choline transporter (CHT1) (h) (aa) | hr[1] (CHO cells) | hemicholinium-3 |
| 5-HT transporter (h) (aa) | hr[1] (CHO cells) | imipramine |

(ag) = agonist radioligand; (aa) = antagonist radioligand;

[1] hr—human recombinant;

[2] ns—non-selective

TABLE 6

| Assay | Ligand | Conc. | Non Specific | Incubation |
|---|---|---|---|---|
| $A_1$ (h) (aa) | [$^3$H]DPCPX | 1 nM | DPCPX (1 μM) | 60 min/22° C. |
| $A_{2A}$ (h)(ag) | [$^3$H]CGS 21680 | 6 nM | NECA (10 μM) | 120 min/22° C. |
| $A_3$ (h) (ag) | [$^{125}$I]AB-MECA | 0.15 nM | IB-MECA (1 μM) | 120 min/22° C. |
| $\alpha_1$ (ns) (aa) | [$^3$H]prazosin | 0.25 nM | prazosin (0.5 μM) | 60 min/22° C. |
| $\alpha_2$ (ns) (aa) | [$^3$H]RX 821002 | 0.5 nM | (−)epinephrine (100 μM) | 60 min/22° C. |
| $\beta_1$ (h) (ag) | [$^3$H](−)CGP 12177 | 0.15 nM | alprenolol (50 μM) | 60 min/22° C. |
| $\beta_2$ (h) (ag) | [$^3$H](−)CGP 12177 | 0.2 nM | alprenolol (50 μM) | 120 min/22° C. |
| $AT_1$ (h) (aa) | [$^{125}$I][Sar$^1$,Ile8]-AT-II | 0.05 nM | angiotensin-II (10 μM) | 120 min/37° C. |
| $AT_2$ (h) (ag) | [$^{125}$I]CGP 42112A | 0.04 nM | angiotensin-II (1 μM) | 180 min/37° C. |
| BZD (central) (ag) | [$^3$H]flunitrazepam | 0.4 nM | diazepam (3 μM) | 60 min/4° C. |
| $B_1$ (h) (ag) | [$^3$H]desArg$^{10}$-KD | 0.35 nM | desArg$^9$[Leu$^8$]-BK (10 μM) | 60 min/22° C. |
| $B_2$ (h) (ag) | [$^3$H]bradykinin | 0.2 nM | bradykinin (1 μM) | 60 min/22° C. |
| $CB_1$ (h) (ag) | [$^3$H]CP 55940 | 0.5 nM | WIN 55212-2 (10 μM) | 120 min/37° C. |
| $CB_2$ (h) (ag) | [$^3$H]WIN 55212-2 | 0.8 nM | WIN 55212-2 (5 μM) | 120 min/37° C. |
| $CCK_1$ ($CCK_A$) (h) (ag) | [$^{125}$I]CCK-8s | 0.08 nM | CCK-8s (1 μM) | 60 min/22° C. |
| $CCK_2$ ($CCK_B$) (h) (ag) | [$^{125}$I]CCK-8s | 0.08 nM | CCK-8s (1 μM) | 60 min/22° C. |
| $CRF_1$ (h) (ag) | [$^{125}$I]sauvagine | 0.075 nM | sauvagine (0.5 μM) | 120 min/22° C. |
| $D_1$ (h) (aa) | [$^3$H]SCH 23390 | 0.3 nM | SCH 23390 (1 μM) | 60 min/22° C. |
| $D_{2S}$ (h) (aa) | [$^3$H]spiperone | 0.3 nM | (+)butaclamol (10 μM) | 60 min/22° C. |
| $D_3$ (h) (aa) | [$^3$H]spiperone | 0.3 nM | (+)butaclamol (10 μM) | 60 min/22° C. |
| $D_{4.4}$ (h) (aa) | [$^3$H]spiperone | 0.3 nM | (+)butaclamol (10 μM) | 60 min/22° C. |
| $ET_A$ (h) (ag) | [$^{125}$I]endothelin-1 | 0.03 nM | endothelin-1 (0.1 μM) | 120 min/37° C. |
| $ET_B$ (h) (ag) | [$^{125}$I]endothelin-1 | 0.03 nM | endothelin-1 (0.1 μM) | 120 min/37° C. |
| GABA (ns) (ag) | [$^3$H]GABA | 10 nM | GABA (100 μM) | 60 min/22° C. |
| AMPA | [$^3$H]AMPA | 8 nM | L-glutamate (1 mM) | 60 min/4° C. |
| kainate (ag) | [$^3$H]kainic acid | 5 nM | L-glutamate (1 mM) | 60 min/4° C. |
| NMDA (aa) | [$^3$H]CGP 39653 | 5 nM | L-glutamate (100 μM) | 60 min/4° C. |
| $H_1$ (h) (aa) | [$^3$H]pyrilamine | 3 nM | pyrilamine (1 μM) | 60 min/22° C. |
| $H_2$ (h) (aa) | [$^{125}$I]APT | 0.075 nM | tiotidine (100 μM) | 120 min/22° C. |
| $H_3$ (h) (ag) | [$^3$H]Nα-Me-histamine | 1 nM | (R)α-Me-histamine (1 μM) | 60 min/22° C. |
| $I_2$ (aa) | [$^3$H]idazoxan (+1 μM yohimbine) | 2 nM | cirazoline (10 μM) | 30 min/22° C. |
| $BLT_1$ ($LTB_4$) (h) (ag) | [$^3$H]$LTB_4$ | 0.2 nM | $LTB_4$ (0.2 μM) | 60 min/22° C. |
| $CysLT_1$ ($LTD_4$) (h) (ag) | [$^3$H]$LTD_4$ | 0.3 nM | $LTD_4$ (1 μM) | 60 min/22° C. |
| GnRH (LH-RH) (ag) | [$^{125}$I][D-Trp$^6$]-LH-RH | 0.05 nM | [D-Trp$^6$]-LH-RH (1μM) | 90 min/4° C. |
| $MC_4$ (h) (ag) | [$^{125}$I]NDP-α-MSH | 0.05 nM | NDP-α-MSH (1 μM) | 120 min/37° C. |
| M (ns) (aa) | [$^3$H]QNB | 0.05 nM | atropine (1 μM) | 120 min/22° C. |
| $NK_1$ (h) (ag) | [$^{125}$I]BH-SP | 0.15 nM | [Sar$^9$,Met($O_2$)$^{11}$]-SP (1 μM) | 60 min/22° C. |
| $NK_2$ (h) (ag) | [$^{125}$I]NKA | 0.1 nM | [Nleu$^{10}$]-NKA (4-10) (10 μM) | 60 min/22° C. |
| $NK_3$ (h) (aa) | [$^3$H]SR 142801 | 0.4 nM | SB 222200 (10 μM) | 120 min/22° C. |
| Y (ns) (ag) | [$^{125}$I]peptide YY | 0.05 nM | NPY (1 μM) | 120 min/22° C. |
| N neuronal α-BGTX-insensitive (α4β2) (ag) | [$^3$H]cytisine | 1.5 nM | nicotine (10 μM) | 75 min/4° C. |
| opioid (ns) (aa) | [$^3$H]naloxone | 1 nM | naloxone (1 μM) | 40 min/22° C. |
| NOP (ORL1) (h) (ag) | [$^3$H]nociceptin | 0.2 nM | nociceptin (1 μM) | 60 min/22° C. |
| PCP (aa) | [$^3$H]TCP | 10 nM | MK 801 (10 μM) | 120 min/37° C. |
| P2X (ag) | [$^3$H]α,β-MeATP | 3 nM | α,β-MeATP (10 μM) | 120 min/4° C. |
| P2Y (ag) | [$^{35}$S]dATPαS | 10 nM | dATPαS (10 μM) | 60 min/22° C. |
| 5-HT (ns) (ag) | [$^3$H]serotonin | 2 nM | serotonin (10 μM) | 60 min/37° C. |
| σ (ns) (aa) | [$^3$H]DTG | 8 nM | haloperidol (10 μM) | 120 min/22° C. |
| $sst_5$ (ag) | [$^{125}$I]Tyr$^{11}$-somatostatin-14 | 0.1 nM | somatostatin-14 (1 μM) | 120 min/22° C. |
| GR (h) (ag) | [$^3$H]dexamethasone | 1.5 nM | triamcinolone (10 μM) | 6 h/4° C. |
| ER (ns) (ag) | [$^3$H]estradiol | 1 nM | 17-β-estradiol (6 μM) | 20 h/4° C. |
| PR (h) (ag) | [$^3$H]progesterone | 0.5 nM | promegestone (1 μM) | 20 h/4° C. |
| TR (TH) (ag) | [$^{125}$I]$T_3$ | 0.1 nM | $T_3$ (1 μM) | 18 h/4° C. |
| $TRH_1$ (h) (ag) | [$^3$H]Me-TRH | 2 nM | TRH (10 μM) | 120 min/4° C. |
| $V_{1a}$ (h) (ag) | [$^3$H]AVP | 0.3 nM | AVP (1 μM) | 60 min/22° C. |
| $V_2$ (h) (ag) | [$^3$H]AVP | 0.3 nM | AVP (1 μM) | 120 min/22° C. |
| $Ca^{2+}$ channel (L, dihydropyridine site) (aa) | [$^3$H]nitrendipine | 0.2 nM | nifedipine (1 μM) | 120 min/22° C. |
| $Ca^{2+}$ channel (L, diltiazem site) (benzothiazepines) (aa) | [$^3$H]diltiazem | 5 nM | diltiazem (10 μM) | 120 min/22° C. |
| $Ca^{2+}$ channel (L, verapamil site) (phenylalkylamine) (aa) | [$^3$H](−)D 888 | 3 nM | D 600 (10 μM) | 120 min/22° C. |
| $K_{ATP}$ channel (aa) | [$^3$H]glibenclamide | 0.1 nM | glibenclamide (1 μM) | 60 min/22° C. |
| hERG (membrane preparation) (aa) | [$^3$H]astemizole | 2 nM | astemizole (10 μM) | 75 min/22° C. |
| $K_V$ channel (aa) | [$^{125}$I]α-dendrotoxin | 0.01 nM | α-dendrotoxin (50 nM) | 60 min/22° C. |
| $SK_{Ca}$ channel (aa) | [$^{125}$I]apamin | 0.007 nM | apamin (100 nM) | 60 min/4° C. |
| $Na^+$ channel (site 2) (aa) | [$^3$H]batrachotoxinin | 10 nM | veratridine (300 μM) | 60 min/22° C. |
| $Cl^-$ channel (GABA-gated) (aa) | [$^{35}$S]TBPS | 3 nM | picrotoxinin (20 μM) | 120 min/22° C. |

TABLE 6-continued

Experimental Conditions

| Assay | Ligand | Conc. | Non Specific | Incubation |
|---|---|---|---|---|
| norepinephrine transporter (h) (aa) | [$^3$H]nisoxetine | 1 nM | desipramine (1 μM) | 120 min/4° C. |
| dopamine transporter (h) (aa) | [$^3$H]BTCP | 4 nM | BTCP (10 μM) | 120 min/4° C. |
| GABA transporter (aa) | [$^3$H]GABA (+10 μM isoguvacine) (+10 μM baclofen) | 10 nM | GABA (1 mM) | 30 min/22° C. |
| choline transporter (CHT1) (h) (aa) | [$^3$H]hemicholinium-3 | 3 nM | hemicholinium-3 (10 μM) | 60 min/22° C. |
| 5-HT transporter (h) (aa) | [$^3$H]imipramine | 2 nM | imipramine (10 μM) | 60 min/22° C. |

(ag) = agonist radioligand; (aa) = antagonist radioligand; (ns)—non-selective

Analysis and Expression of Results: Compounds of the invention were tested in the biochemical assays and percent inhibition of specific binding was determined. The specific ligand binding to the receptors is defined as the difference between the total binding and the nonspecific binding determined in the presence of an excess of unlabelled ligand. The results are expressed as a percent inhibition of control specific binding (100−((measured specific binding/control specific binding)×100)) obtained in the presence of test compounds. The results of the assays are summarized in Table 7.

TABLE 7

Results of Binding Assays

| | % Inhibition of Control Specific Binding @ 10 μM | | | |
|---|---|---|---|---|
| | (MI) | (MII) | (MIII) | (MIV) |
| $A_1$ (h) (aa) | 10 | 9 | 2 | 6 |
| $A_{2A}$ (h) (ag) | 10 | −5 | 2 | 3 |
| $A_3$ (h) (ag) | 69 | 17 | 11 | 50 |
| $α_1$ (ns) (aa) | −4 | −7 | −5 | −3 |
| $α_2$ (ns) (aa) | −7 | −9 | −7 | −7 |
| $β_1$ (h) (ag) | −2 | −7 | 2 | 3 |
| $β_2$ (h) (ag) | 6 | −3 | −6 | −10 |
| $AT_1$ (h) (aa) | 11 | 0 | 6 | 0 |
| $AT_2$ (h) (aa) | −1 | −6 | −2 | 1 |
| BZD (central) (ag) | −35 | −37 | −20 | −29 |
| $B_1$ (h) (ag) | 0 | 6 | 5 | 4 |
| $B_2$ (h) (ag) | 2 | −12 | −3 | 0 |
| $CB_1$ (h) (ag) | −20 | 11 | 6 | 4 |
| $CB_2$ (h) (ag) | −2 | 1 | −3 | 1 |
| $CCK_1$ ($CCK_A$) (h) (ag) | 47 | 0 | −14 | 25 |
| $CCK_2$ ($CCK_B$) (h) (ag) | −10 | −18 | −18 | −12 |
| $CRF_1$ (h) (ag) | −4 | 1 | −9 | −23 |
| $D_1$ (h) (aa) | −18 | −14 | −17 | −17 |
| $D_{2S}$ (h) (aa) | −16 | −8 | −22 | −17 |
| $D_3$ (h) (aa) | 7 | 11 | 0 | 7 |
| $D_{4.4}$ (h) (aa) | 1 | 9 | 13 | −15 |
| $ET_A$ (h) (ag) | −21 | −16 | −12 | −27 |
| $ET_B$ (h) (ag) | −7 | −4 | 0 | −3 |
| GABA (ns) (ag) | −12 | 0 | −10 | 5 |
| AMPA (ag) | 1 | −10 | −2 | −4 |
| kainate (ag) | −4 | −21 | −10 | −8 |
| NMDA (aa) | 2 | 5 | 0 | −41 |
| $H_1$ (h) (aa) | −8 | 2 | −2 | −11 |
| $H_2$ (h) (aa) | −41 | −27 | −19 | −20 |
| $H_3$ (h) (ag) | −3 | −2 | −13 | −4 |
| $I_2$ (aa) | 28 | 22 | 20 | 8 |
| $BLT_1$ ($LTB_4$) (h) (ag) | −15 | −8 | −4 | −6 |
| $CysLT_1$ ($LTD_4$) (ag) | 3 | 18 | 11 | 11 |
| GnRH (LH-RH) (ag) | −21 | −51 | 5 | 0 |
| $MC_4$ (h) (ag) | −23 | −25 | −11 | −15 |
| M (ns) (aa) | 18 | 1 | 20 | 25 |
| $NK_1$ (h) (ag) | −7 | 9 | −9 | −7 |
| $NK_2$ (h) (ag) | −6 | −3 | 0 | 2 |
| $NK_3$ (h) (aa) | −11 | 3 | −2 | −7 |

TABLE 7-continued

Results of Binding Assays

| | % Inhibition of Control Specific Binding @ 10 μM | | | |
|---|---|---|---|---|
| | (MI) | (MII) | (MIII) | (MIV) |
| Y (ns) (ag) | −6 | −6 | −2 | −2 |
| N neuronal α-BGTX-insensitive (α4β2) (ag) | 0 | −3 | −11 | −3 |
| opioid (ns) (aa) | −6 | −14 | −15 | −10 |
| NOP (ORL1) (h) (ag) | −10 | −4 | 0 | −2 |
| PCP (aa) | 0 | 5 | 2 | 4 |
| P2X (ag) | 4 | 4 | 2 | 2 |
| P2Y (ag) | −19 | −2 | −1 | 0 |
| 5-HT (ns) (ag) | 21 | 14 | −12 | 6 |
| σ (ns) (ag) | 20 | 39 | 34 | 50 |
| $sst_5$ (h) (ag) | −25 | 16 | 2 | −7 |
| GR (h) (ag) | 5 | 30 | 0 | 4 |
| ER (ns) (h) (ag) | −8 | 3 | −2 | −11 |
| PR (h) (ag) | 23 | 74 | 8 | 11 |
| TR (TH) (ag) | −7 | 0 | −9 | −2 |
| $TRH_1$ (h) (ag) | 18 | −4 | −5 | 0 |
| $V_{1a}$ (h) (ag) | 2 | 15 | −1 | −8 |
| $V_2$ (h) (ag) | 5 | 3 | 4 | −1 |
| $Ca^{2+}$ channel (L, dihydropyridine site) (aa) | 16 | 18 | −2 | 16 |
| $Ca^{2+}$ channel (L, diltiazem site) (benzothiazepines) (aa) | 2 | 22 | −2 | 1 |
| $Ca^{2+}$ channel (L, verapamil site) (phenylalkylamine) (aa) | −2 | −13 | −1 | −5 |
| $K_{ATP}$ channel (aa) | 17 | 24 | 7 | 7 |
| hERG (membrane preparation) (aa) | −39 | 7 | 8 | 10 |
| $K_V$ channel (aa) | −2 | −3 | −2 | −4 |
| $SK_{Ca}$ channel (aa) | −6 | 4 | 1 | −10 |
| $Na^+$ channel (site 2) (aa) | −5 | 13 | 1 | 5 |
| $Cl^−$ channel (GABA-gated) (aa) | 47 | 81 | 38 | 36 |
| norepinephrine transporter (h) (aa) | 56 | −13 | 9 | 20 |
| dopamine transporter (h) (aa) | 32 | 23 | 13 | 7 |
| GABA transporter (aa) | −16 | 7 | −35 | −24 |
| choline transporter (CHT1) (h) (aa) | −16 | −22 | −13 | 10 |
| 5-HT transporter (h) (aa) | 1 | 16 | 13 | 18 |

(ag) = agonist radioligand; (aa) = antagonist radioligand; (ns)—non-selective

In Vitro Pharmacology results: Results showing an inhibition (or stimulation for assays run in basal conditions) greater than 50% are generally considered to represent significant effects of the test compounds. Results showing an inhibition (or stimulation) between 20% and 50% are generally indicative of weaker to moderate effects. Results showing an inhibition (or stimulation) lower than 20% are generally considered less significant.

The biology of selected targets is summarized as follows. Adenosine A3 receptor: G-protein coupled receptor with a poorly defined role in cardiac, inflammatory and neuronal cell functions (Fishman, et al. "Pharmacology and therapeutic applications of A3 receptor subtype." Curr. Top. Med. Chem. (2003), 3(4):463-9); Cannabinoid $CB_2$ receptor: G-protein coupled receptor involved in nociception, and immune cell function (Jhaveri, et al. "Cannabinoid $CB_2$ receptor-mediated anti-nociception in models of acute and chronic pain." Mol Neurobiol. (2007), 36(1):26-35; Marriott, et al. "Recent advances in the development of selective ligands for the cannabinoid CB(2) receptor." Curr. Top. Med. Chem. (2008), 8(3):187-204); Cl⁻ channel (rat): GABA-gated chloride channel regulates neuronal cell activity (Treiman, D. "GABAergic Mechanisms in Epilepsy." Epilepsia (2001), 42(3):8-12); Adrenergic α1 (non-selective, rat): G protein-coupled receptor for catecholamines. These receptors regulate smooth muscle contraction and neurotransmitter release (Michelotti, et al. "Alpha 1-Adrenergic receptor regulation: basic science and clinical implications." Pharmacol. Ther. (2000), 88(3):281-309); Sigma (non-selective): Membrane bound CNS receptor modulating behavior related to depression (Stahl, S. "Antidepressant Treatment of Psychotic Major Depression: Potential Role of the Sigma Receptor." CNS Spectr. (2005), 10(4):319-323); Norepinephrine transporter: Transports noradrenaline and to a lesser extent dopamine from the synapse back to intraneuronal vesicles for storage until later use (Mandela, et al. "The Norepinephrine Transporter and Its Regulation." J. Neurochemistry (2006), 97(2): 310-333); Progesterone PR: Expressed in all major physiological systems, with peaks in uterus/ovary, cerebellum, spinal cord and hypothalamus (Edwards, et al. "Progesterone receptor transcription and non-transcription signaling mechanisms." Steroids (2003), 68(10-13):761-770).

Example B2

In-Vitro Pharmacology: Human Androgen Receptor (AR) Binding

Tissue Preparation: The human androgen receptor was expressed in LNCAP cells which were cultured and harvested by trypsinization from T-175 flasks. The frozen pellet was thawed and resuspended by sonication, then diluted to the appropriate concentration. The homogenate was centrifuged @ 48,000 g for 10 min at 4° C. The supernatant was used. The protein was determined. The tissue was diluted to 0.325 mg/mL with assay buffer so that each tube received 65 μg of protein, or the final assay concentration was 0.260 mg/mL.

Materials and Reagents: [³H]-Methyltrienolone was diluted to a concentration of 5 nM in 25 mM HEPES pH 7.4 (containing 1.0 mM EDTA, 10 mM sodium molybdate, 10% glycerol, 0.5 mM PMSF) such that the final radioligand concentration in the assay was 0.5 nM. Non-specific binding is defined as that remaining in the presence of $2 \times 10^{-7}$ M Methyltrienolone (R1881). The reference compound was Methyltrienolone (R1881), run at the following final concentrations of: $2 \times 10^{-11}$, $5 \times 10^{-11}$, $1 \times 10^{-10}$ $2 \times 10^{-10}$, $5 \times 10^{-10}$, $1 \times 10^{-9}$ $2 \times 10^{-9}$, $5 \times 10^{-9}$, $1 \times 10^{-8}$, $2 \times 10^{-8}$, $5 \times 10^{-8}$ and $1 \times 10^{-7}$ M.

Buffers: 25 mM HEPES pH7.4; 1.0 mM EDTA; 10 mM sodium molybdate; 10% Glycerol; 0.5 mM PFSM (dissolved PMSF in EtOH first, before adding to remaining buffer).

Binding Reaction: (Liao, et al. "The Use of a Hydroxylapatite-Filter Steroid Receptor Assay Method in the Study of the Modulation of Androgen Receptor Interaction." J. Steroid Biochem. (1984), 20:11-17 (with modifications)). Each vial received the following components: test/reference compound or vehicle (25 μL); [³H]-Methyltrienolone (25 μL); tissue suspension (200 μL). The binding reaction was initiated with the addition of tissue, and was incubated at 0-4° C. (in refrigerator) for 18-22 h (overnight). The binding reaction was terminated by rapid filtration of the tube contents onto 0.1% PEI treated GF/B filters. The assay tubes were rinsed once with ice-cold 25 nM HEPES, then rapidly rinsed with 6×1 mL/tube of the same wash buffer. Radioactivity trapped on the filters was assessed using liquid scintillation spectrophotometry after soaking the filers for at least 1 h in scintillation cocktail. Non-specific binding is defined as the amount of radioactivity remaining in the presence of $2 \times 10^{-7}$ M unlabeled Methyltrienolone (R1881). Specific binding was calculated from the difference between the total and non-specific binding. $IC_{50}$ values were determined by plotting specific binding as a function of test-compound concentration. Ki values were obtained directly from the $IC_{50}$ values using the Cheng-Prusoff equation ($Ki = IC_{50}/(1+(L/K_D))$), where L=concentration of radioligand in the assay, and $K_D$=affinity of the radioligand for the receptor determined independently. Examples of assay results are shown in Table 8.

TABLE 8

AR Binding Activity of Compounds (MI)-(MIV)

| | $K_1$ (μM) Reference Compound | | |
|---|---|---|---|
| Test Compound | Mibolerone | Mibolerone Reference Compound $K_1$ | Methyltrienolone |
| | 0.0051 | 0.0051 | 0.000063 |
| (MI) | NR | NR | NR (>10) |
| (MII) | 0.074 | 0.051 | 0.059 |
| (MIII) | 0.83 | 1.5 | 0.314 |
| (MIV) | 0.69 | 0.97 | 0.361 |

The data in the Table 8 shows that the compounds MII-MIV have activity towards androgen receptor.

Example B3

In-Vitro Pharmacology: Enzyme Assays

The enzyme assays provided below will be familiar to those skilled in the art. For each enzyme assay, the general procedures and experimental conditions are summarized in Tables 9 and 10, respectively.

TABLE 9

General Procedures

| Assay | Origin | Reference Compound |
|---|---|---|
| PDE1B (h) | human recombinant (Sf9 cells) | calmidazolium |
| PDE2A (h) | human recombinant (Sf9 cells) | EHNA |
| PDE3A (h) | human recombinant (Sf9 cells) | milrinone |
| PDE4D (h) | human recombinant (Sf9 cells) | rolipram |
| PDE5 (h) (ns) | human platelets | zaprinast |
| adenylyl cyclase (basal) | rat brain | forskolin |

TABLE 9-continued

General Procedures

| Assay | Origin | Reference Compound |
|---|---|---|
| guanylyl cyclase (basal) | bovine lung | sodium nitroprusside |
| PKCα (h) | human recombinant (insect cells) | Bis 10 |
| acetylcholinesterase (h) | human recombinant (HEK-293 cells) | neostigmine |
| COMT | porcine liver | Ro 41-0960 |
| GABA transaminase | rat brain | AoAA |
| MAO-A (h) | human placenta | clorgyline |
| MAO-B (h) | human platelets | deprenyl |
| PNMT | bovine adrenal medulla | LY 78335 |
| tyrosine hydroxylase | rat striatum | 3-iodo L-tyrosine |
| ATPase (Na$^+$/K$^+$) | porcine cerebral cortex | ouabain |

(ns)—non-selective

TABLE 10

Experimental Conditions

| Assay | Substrate/Stimulus/Tracer | Incubation | Reaction Product | Method of Detection |
|---|---|---|---|---|
| PDE1B (h) | cGMP (240 nM) | 30 min/22° C. | residual cGMP | HTRF |
| PDE2A (h) | cAMP (40 nM) | 30 min/22° C. | residual cAMP | HTRF |
| PDE3A (h) | cAMP (40 nM) | 30 min/22° C. | residual cAMP | HTRF |
| PDE4D (h) | cAMP (40 nM) | 30 min/22° C. | residual cAMP | HTRF |
| PDE5 (h) (ns) | cGMP (240 nM) | 30 min/22° C. | residual cGMP | HTRF |
| adenylyl cyclase (basal) | ATP (0.5 mM) (300 μM forskolin for control) | 60 min/30° C. | cAMP | HTRF |
| guanylyl cyclase (basal) | GTP (0.1 mM) (1 mM sodium nitroprusside for control) | 90 min/30° C. | cGMP | HTRF |
| PKCα (h) | ATP + biotinyl-neurogranin 28-43 peptide (60 nM) | 15 min/22° C. | phosphobiotinyl-neurogranin 28-43 peptide | HTRF |
| acetylcholinesterase(h) | AMTCh (50 μM) | 30 min/37° C. | thio-conjugate | Photometry |
| COMT | Esculetin (1 μM) | 30 min/37° C. | scopoletin | Fluorimetry |
| GABA transaminase | GABA (9 mM) + α-ketoglutarate (9 mM) | 60 min/37° C. | succinic semialdehyde | Fluorimetry |
| MAO-A (h) | Kynuramine (0.15 mM) | 30 min/30° C. | 4-OHquinoline | Photometry |
| MAO-B (h) | Benzylamine (0.5 mM) | 45 min/37° C. | benzaldehyde | Photometry |
| PNMT | [14C]SAM (4 μM) + normetanephrine (28 mM) | 20 min/37° C. | [$^{14}$C]metanephrine | Scintillation counting |
| tyrosine hydroxylase | [3H]tyrosine (10 μM) | 40 min/37° C. | [$^3$H]H$_2$O | Scintillation counting |
| ATPase (Na+/K+) | ATP (2 mM) | 60 min/37° C. | Pi | Photometry |

(ns)—non-selective

Analysis and Expression of Results: The results are expressed as a percent of control specific activity ((measured specific activity/control specific activity)×100) obtained in the presence of the test compounds. The results are presented in Table 11.

TABLE 11

Results of Enzyme Assays

| Assay | (MI) | (MII) | (MIII) | (MIV) |
|---|---|---|---|---|
| | % Inhibition of Control Values @ 10 μM | | | |
| PDE1B (h) | 0 | −11 | −8 | −2 |
| PDE2A (h) | 12 | 2 | 2 | 0 |
| PDE3A (h) | 3 | 0 | 4 | 2 |
| PDE4D (h) | 1 | −9 | −11 | −41 |

TABLE 11-continued

Results of Enzyme Assays

| Assay | (MI) | (MII) | (MIII) | (MIV) |
|---|---|---|---|---|
| PDE5 (h) (ns) | 4 | −1 | 8 | 2 |
| PKCα (h) | 4 | 6 | 3 | 5 |
| acetylcholinesterase (h) | 51 | 9 | −1 | 23 |
| COMT | 1 | −1 | −1 | 0 |
| GABA transaminase | −7 | −5 | −2 | −1 |
| MAO-A (h) | −5 | 0 | 14 | 11 |
| MAO-B (h) | 8 | −4 | −5 | 11 |
| PNMT | −6 | −4 | −2 | 14 |
| tyrosine hydroxylase | −4 | 2 | −2 | −2 |
| ATPase (Na$^+$/K$^+$) | 4 | −10 | 3 | −13 |
| | % Stimulation Relative to Control @ 10 μM | | | |
| adenylyl cyclase (basal) | 0 | 3 | 4 | 11 |
| guanylyl cyclase (basal) | 0 | 0 | −1 | 2 |

(ns)—non-selective

Example B4

Androgen Receptor Nuclear Translocation Assay

Cell Handling: PathHunter NHRPro cell lines were expanded from freezer stocks in T25 flasks according to standard procedures and maintained in selective growth media prior to assay. Once it was established that the cells were healthy and growing normally, cells were transferred from flasks using trypsin-free cell dissociation buffer and seeded into white walled clear bottom 384-well microplates for compound profiling. For profiling, cells were seeded at a density of 10,000 cells per well in a total volume of 50 μL and were allowed to adhere and recover overnight prior to compound addition. Media contained charcoal-dextran filtered serum to reduce the level of hormones present.

Screening Mode: The compounds were tested in agonist and antagonist modes in the following dose responses: 60, 20, 6.67, 2.22, 0.74, 0.25, 0.08, 0.03, 0.009 and 0.003 µM, in duplicate, with three-fold serial dilutions, and obtaining $EC_{50}$ and $IC_{50}$ output.

Agonist Format: Intermediate dilution of compound stocks were generated such that 5.5 µL of 10× compound could be added to each well with a final DMSO concentration of 1% of total volume. For profiling compound in agonist mode, the cells were incubated in the presence of compound at 37° C. for 5 h.

Antagonist Format: Agonist dose curves were performed to determine the $EC_{80}$ value for the following antagonist testing with compounds. 5.5 µL of 10× agonist was added to each well with an equal concentration of vehicle present. $EC_{80}$ agonist concentration was determined directly from agonist dose curve. For antagonist determination, cells were pre-incubated with antagonist followed by agonist challenge at the $EC_{80}$ concentration: 5.5 µL of 10× compound added to cells and incubated at 37° C. for 1 h; 5.5 µL of 11×$EC_{80}$ agonist added to cells and incubated at 37° C. for 5 h.

Signal Detection: After appropriate compound incubation, assay signal was generated through a single addition of 30 µL (50% v/v) of PathHunter Detection reagent cocktail for agonist and antagonist assays respectively followed by 1 h incubation at room temperature. Microplates were read following signal generation with a PerkinElmer ViewLux™ instrument for chemiluminescent signal detection.

Data Analysis: Dose curves in the presence and absence of compound were plotted using GraphPad Prism. A summary of the assay results is provided in Table 12.

TABLE 12

Androgen Receptor Nuclear Translocation assay results for compounds (MI)-(MIV)

| | AR Nuclear Translocation Assay | |
|---|---|---|
| | Agonist Mode $EC_{50}$ µM | Antagonist Mode $IC_{50}$ µM |
| Norgesterol (ag) | 0.0029 | |
| Geldanamycin (aa) | | 0.018 |
| (MI) | NR | >60 |
| (MII) | NR | 3.2 |
| (MIII) | NR | 16.2 |
| (MIV) | NR | 11.6 |

(ag) = agonist; (aa) = antagonist

Example B5

$GABA_A$ Functional Assay

The aim of this study was to evaluate the functional effects of MI-MIV at the human ionotropic $GABA_A$ receptors. The human $GABA_A$ α1β3 and α1β3γ2 receptors were expressed in *Xenopus* oocytes. Effects of acute exposure were used to assess the possible agonistic effects of compounds while pre- and co-exposure with GABA was used to evaluate the possible inhibitory effects of the compounds.

Oocytes preparation: All experiments were carried out at human $GABA_A$ expressed in *Xenopus* oocytes using the method of cDNA expression. *Xenopus* oocytes were prepared and injected using standard procedures. Briefly, ovaries were harvested from *Xenopus Laevis* females that had been deeply anesthetized and pitted following the animal rights rule from the Geneva canton. A small piece of ovary was isolated for immediate preparation while the remaining part was placed at 4° C. in a sterile Barth solution containing NaCl (88 mM), KCl (1 mM), $NaHCO_3$ (2.4 mM), HEPES (10 mM), $MgSO_4.7H_2O$ (0.82 mM), $Ca(NO_3)_2.4H_2O$ (0.33 mM), $CaCl_2.6H_2O$ (0.41 mM), at pH 7.4, and supplemented with 20 µg/mL of kanamycine, 100 unit/mL penicillin and 100 µg/mL streptomycin. All recordings were performed at 18° C. and cells superfused with OR2 medium containing NaCl (82.5 mM), KCl (2.5 mM), HEPES (5 mM), $CaCl_2.2H_2O$ (1.8 mM), $MgCl_2.6H_2O$ (1 mM), pH 7.4.

Electrophysiological recordings: Currents evoked by GABA were recorded using an automated process equipped with standard two-electrode voltage-clamp configuration (TVEC). Unless indicated, cells were held at −80 mV. Data were captured and analyzed using a HiQScreen proprietary data acquisition and analysis software running under Matlab (Mathworks Inc.).

Agonist Preparation: GABA was prepared as a concentrated stock solution ($10^{-1}$ M) in water and then diluted in the recording medium to obtain the desired test concentration. Compounds were prepared as stock solution ($10^{-2}$ M) in DMSO and then diluted in the recording medium to obtain the desired test concentration. Residual DMSO did not exceed the concentration of 1% a concentration that has been shown to have no effects on *Xenopus* oocytes function.

Data Analysis and Statistics: For statistical analysis values were computed either with Excel (Microsoft) or Matlab (Mathworks Inc.). To obtain statistical significance all experiments were carried out using at least three cells. Values are presented as mean±SEM.

Experimental Procedures: Injections of cDNAs encoding for the human $GABA_A$ subunits were performed in at least one hundred oocytes using a proprietary automated injection device (Hogg et al., J. Neurosci. Methods, 2008) and receptor expression examined at least two days later. Oocytes were poked with two electrodes and their membrane potential maintained at a fixed value (−80 mV) throughout the experiment.

Measurement of Agonist Activity of MI-MIV: The effects of MI-MIV on $GABA_A$ receptor function was evaluated with a protocol of single exposure (30 sec). In this protocol the cell is first challenged with a reference test pulse of GABA (10 µM, 5 sec) and its response is used as control. GABA is removed and the cell is then exposed for 30 sec to the test compound, during which time channel recordings are measured. Finally the test compound is removed and GABA is reapplied (3 µM, 5 sec) at the end of the incubation. The recordings taken during the 30 sec period when MI-MIV were present showed no detectable inward currents indicating that these compounds do not activate the α1β3 $GABA_A$ receptor. M4 was likewise tested for agonist activity at the α1β3γ2 $GABA_A$ receptor. Similar to the results obtained for the α1β3 $GABA_A$ receptor, M4 did not evoke any detectable inward currents at the α1β3γ2 $GABA_A$ receptor, indicating that these compounds do not activate either form of the $GABA_A$ receptor.

Measurement of Antagonist Activity of MI-MIV: To evaluate the possible inhibitory effects of MI-MIV concentration inhibition protocols were designed. In this protocol oocytes expressing robust GABA responses are exposed for 45 sec to a given concentration of the compound under scrutiny and the response to a fixed GABA concentration applied in presence of the compound is recorded. Following a brief wash to remove GABA the cell is returned for another 45 sec in the same concentration and the process is then repeated with a higher concentration of the compound. As oocytes are continuously exposed to the test compound a cumulative effect is observed for the highest concentrations. The positive control in this assay, the antagonist tert-butylbicyclophosphorothionate (TBPS), demonstrated a concentration dependent inhibitory effect at the α1β3 receptor. The derived IC$_{50}$ for TBPS was 0.6±0.06 μM. This IC$_{50}$ value is consistent with what has been reported in the literature [Hamann et al, Mol. Pharmacol. (1990), 37(4):578-582].

Results: M1 demonstrated a concentration-dependent inhibition of the α1β3 receptor and the α1β3γ2 receptor with derived IC$_{50}$ values of 20.7±6 04 and 68.3±6.0 μM. At the highest concentration, almost complete inhibition (75±18.4%) was achieved. M2 demonstrated a concentration-dependent inhibition of the α1β3 receptor with a derived IC$_{50}$ value of 2.3±0.3 μM. At the highest concentration, almost complete inhibition (80±10%) was achieved. M3 demonstrated a concentration-dependent inhibition of the α1β3 receptor with a derived IC$_{50}$ value of 4.0±3.15 μM. At the highest concentration, partial inhibition (57±7%) was achieved. M4 demonstrated a concentration-dependent inhibition of the α1β3 receptor with a derived IC$_{50}$ value of 1.55±0.19 μM. At the highest concentration, almost complete inhibition (78±3%) was achieved.

Summary: Agonist Effects: Brief exposure to MI-MIV caused no detectable inward currents at either the α1β3 or the αβ3γ2 GABA$_A$ receptor indicating that these compounds do not activate either of these two forms of the GABA$_A$ receptor. Antagonist Effects: MI-MIV antagonized the α1β3 GABA$_A$ receptor with IC$_{50}$ values and % Inhibition values as summarized in Table 13. As inhibition was observed in the μM range, these data indicate that MI-MIV are functional antagonists of the GABA$_A$ receptor.

TABLE 13

GABA$_A$ Functional Assay results for MI-MIV

| Compound | α1β3 GABA$_A$ | |
|---|---|---|
| | IC$_{50}$ (μM) | % Inhibition @ 100 μM |
| M1 | 20.7 ± 6.03 | 90 |
| M2 | 2.3 ± 1.5 | 88 |
| | 75 ± 2.1 | |
| M3 | 4.0 ± 3.15 | 57 |
| M4 | 1.55 ± 0.19 | 78 |
| | 44.98 ± 4.62 | |

Example B6

Identification of (MI)-(MV) in Rat Plasma

Metabolites of RD162' were isolated and identified in steady-state plasma samples from three male Sprague Dawley rats that were dosed orally with a mixture of non-radiolabeled RD162' and radiolabeled RD162' ([14C]RD162') at 100 mg/kg/day (total RD162') and 250 μCi/kg/day ([14C] radioactivity). The rats were dosed once a day for seven consecutive days; four hours after dosing on the seventh day, plasma was collected from all three rats. The plasma samples were stored at approximately −70° C. or colder.

The [14C] RD162' had a specific activity of 57.6 mCi/mmol and, per HPLC analysis, was >98% pure. The position of the [14C] atom is shown below, where * signifies the position of the radiolabel:

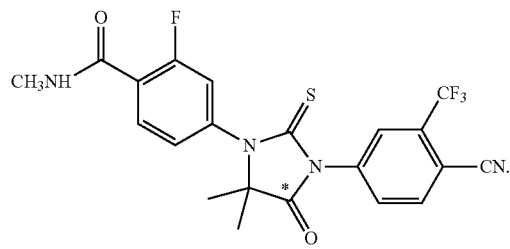

The plasma samples from the three animals were combined in a 1:1:1 mixture (referred to as "Pooled Rat Plasma") and analyzed for concentrations of RD162' and its metabolites. Identification of [14C]RD162' and [14C]RD162' metabolites in Pooled Rat Plasma was based on HPLC co-elution with the reference standards and on mass spectral analyses. Positive ion electrospray LC/MS and LC/MS/MS were used to analyze the metabolites.

To prepare the Pooled Rat Plasma for HPLC analysis, approximately 1 g of the plasma sample was combined with acetonitrile (ACN, sample:ACN, 1:3, v:v), vortex mixed, sonicated in cold water, centrifuged, and the supernatants were removed. The extraction was repeated twice and the respective supernatants were combined. Duplicate aliquots were analyzed by liquid scintillation counting (LSC) to determine the extraction recovery, which was 100%. The combined supernatants were evaporated to dryness and reconstituted in 1 mL of 0.1% formic acid in reverse osmosis (RO) water:ACN: methanol (MeOH, 50:45:5, v:v:v). The sample was vortex mixed, sonicated, microfuged, and duplicate aliquots were analyzed by LSC to determine the reconstitution recovery, which was 98.1%. The reconstituted sample was analyzed by HPLC to determine the metabolite profile with fractions collected at 10-second intervals and analyzed by solid scintillation counting.

The prepared samples were analyzed using the following LC/MS/MS conditions: HPLC: Hewlett Packard 1100 series; Mobile Phase: 0.1% formic acid in reverse osmosis water (A) and acetonitrile (B); Column: Agilent Eclipse XDB-C18, 4.6×150 mm, 5 μm; Guard column: Phenomenex Security Guard Cartridge C18, 3×4 mm; Column temperature: 20° C.; Gradient: 20-80% B in 40 min; Flow Rate: 1.5 mL/min.

For the co-elution experiments, the elution times were determined for RD162' and its metabolites. RD162' and metabolites (MI), (MII), (MIII), (MIV) and (MV) were injected onto the HPLC and the time of elution from the column was measured by ultraviolet light detection at 254 nm. The resulting retention times, which are summarized in Table 14, were used to qualitatively determine the entities

TABLE 14

HPLC Chromatographic Percent of Sample Radioactivity as [14C]RD162' or Metabolites of [14C]RD162' in Pooled Plasma Samples at Steady State with Oral Administration of [14C]RD162' in Male Rats

| Name | Start (mins) | End (mins) | Retention (mins) | Peak Height (mV) | Peak Area (mV) | % Recovered Radioactivity (%) | % Injected Radioactivity (%) |
|---|---|---|---|---|---|---|---|
| (MIII) | 14.67 | 15.33 | 14.97 | 77 | 426 | 12.50 | 7.96 |
| (MV) | 15.60 | 16.30 | 15.93 | 49 | 308 | 9.05 | 5.76 |
| (MIV) | 17.37 | 18.10 | 17.70 | 63 | 452 | 13.27 | 8.45 |
| (MII) | 18.57 | 19.17 | 18.90 | 43 | 288 | 8.45 | 5.38 |

TABLE 14-continued

HPLC Chromatographic Percent of Sample Radioactivity as [14C]RD162'
or Metabolites of [14C]RD162' in Pooled Plasma Samples at Steady
State with Oral Administration of [14C]RD162' in Male Rats

| Name | Start (mins) | End (mins) | Retention (mins) | Peak Height (mV) | Peak Area (mV) | % Recovered Radioactivity (%) | % Injected Radioactivity (%) |
|---|---|---|---|---|---|---|---|
| RD162' | 22.27 | 23.13 | 22.63 | 164 | 1159 | 34.03 | 21.66 |
| (MI) | 24.03 | 24.93 | 24.50 | 86 | 589 | 17.31 | 11.02 |

The structures of (MI), (MII), (MIII), (MIV) and (MV) were confirmed by mass spectral analysis.

B7

Determination of $IC_{50}$ and/or $EC_{50}$ Values

Compounds of the invention may be further assessed by determining $IC_{50}$ and/or $EC_{50}$ values from concentration-response curves. Method of determining the $IC_{50}$ and/or $EC_{50}$ values may be carried out according to known methods.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

All references throughout, such as publications, patents, patent applications and published patent applications, are incorporated herein by reference in their entireties.

What is claimed is:

1. A method of treating prostate cancer, comprising administering to an individual in need thereof a pharmaceutical composition comprising a unit dosage amount of a compound of the formula I:

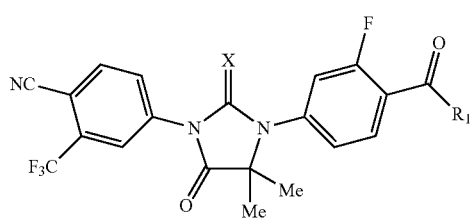

(I)

wherein X is S or O, and
when X is S then $R^1$ is OH or $NH_2$; and
when X is O then $R^1$ is OH, $NH_2$ or NHMe,
or a pharmaceutically acceptable salt or solvate thereof.

2. The method of claim 1, wherein X is S and $R^1$ is OH or $NH_2$.

3. The method of claim 1, wherein X is O and $R^1$ is OH, $NH_2$ or NHMe.

4. The method of claim 1, wherein the compound is

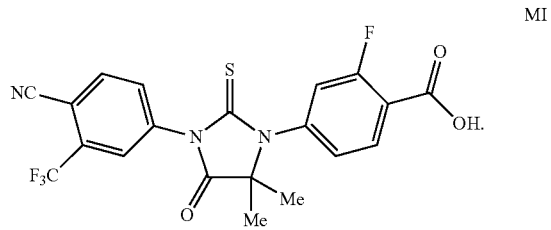 [SMILES: CC1(C)C(=O)N(c2ccc(C#N)c(C(F)(F)F)c2)C(=S)N1c1ccc(C(=O)O)c(F)c1]

MI

5. The method of claim 1, wherein the compound is:

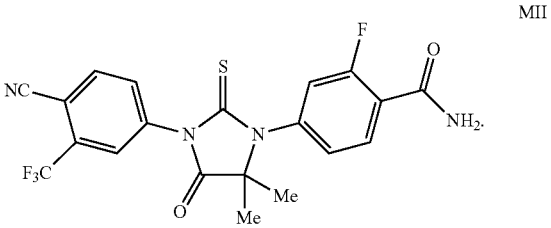 [SMILES: CC1(C)C(=O)N(c2ccc(C#N)c(C(F)(F)F)c2)C(=S)N1c1ccc(C(N)=O)c(F)c1]

MII

6. The method of claim 1, wherein the compound is:

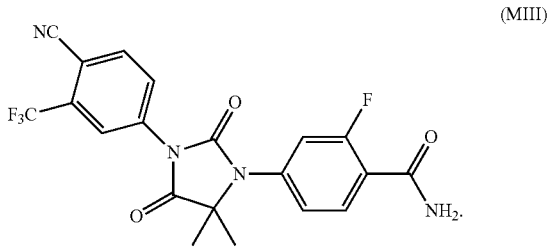 [SMILES: CC1(C)C(=O)N(c2ccc(C#N)c(C(F)(F)F)c2)C(=O)N1c1ccc(C(N)=O)c(F)c1]

(MIII)

7. The method of claim 1, wherein the compound is:

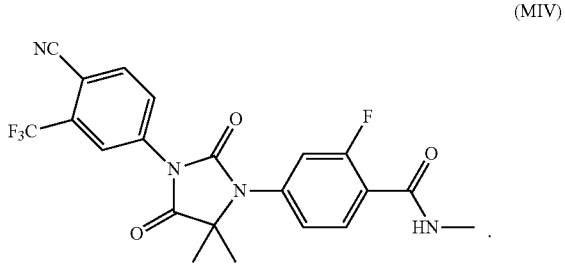 [SMILES: CNC(=O)c1ccc(N2C(=O)N(c3ccc(C#N)c(C(F)(F)F)c3)C(=O)C2(C)C)cc1F]

(MIV)

8. The method of claim 1, wherein the compound is:

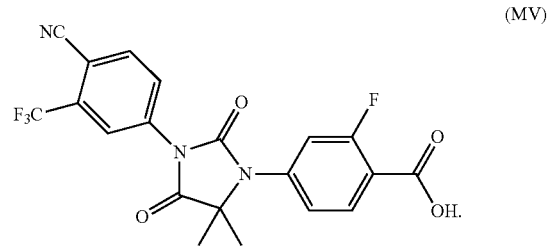 [SMILES: CC1(C)C(=O)N(c2ccc(C#N)c(C(F)(F)F)c2)C(=O)N1c1ccc(C(=O)O)c(F)c1]

(MV)

9. The method of claim 1, wherein the pharmaceutical composition is administered orally.

10. A pharmaceutical composition, comprising:
(a) a unit dosage amount of a compound of the formula I:

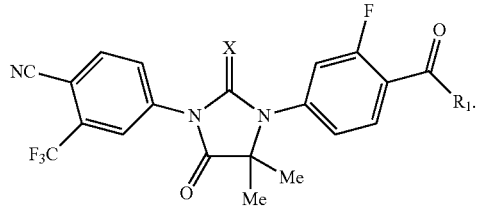

(I)

wherein X is S or O, and
when X is S then $R^1$ is OH or $NH_2$; and
when X is O then $R^1$ is OH, $NH_2$ or NHMe,
or a pharmaceutically acceptable salt or solvate thereof; and
(b) a pharmaceutically acceptable vehicle.

11. The pharmaceutical composition of claim 10, wherein X is S and $R^1$ is OH or $NH_2$.

12. The pharmaceutical composition of claim 10, wherein X is O and $R^1$ is OH, $NH_2$ or NHMe.

13. The pharmaceutical composition of claim 10, wherein the compound is

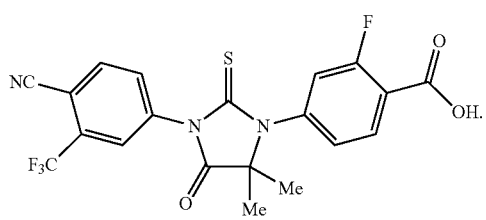

MI

14. The pharmaceutical composition of claim 10, wherein the compound is:

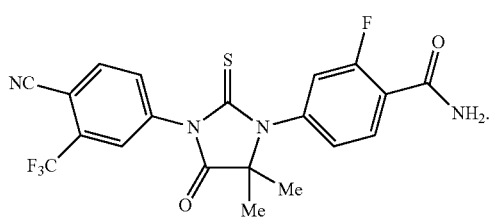

MII

15. The pharmaceutical composition of claim 10, wherein the compound is:

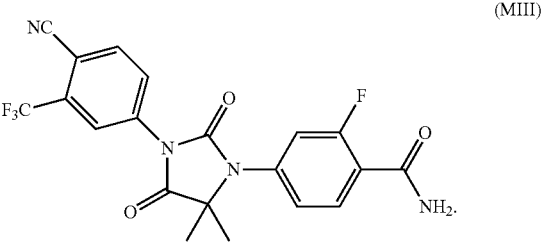 [SMILES: CC1(C)C(=O)N(c2ccc(C#N)c(C(F)(F)F)c2)C(=O)N1c1ccc(C(N)=O)c(F)c1]

(MIII)

16. The pharmaceutical composition of claim 10, wherein the compound is:

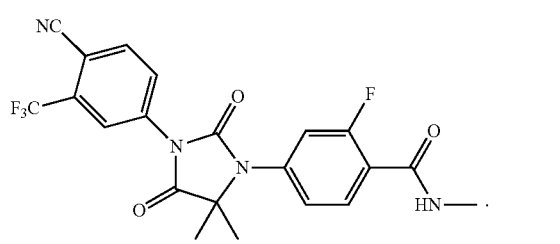

(MIV)

17. The pharmaceutical composition of claim 10, wherein the compound is:

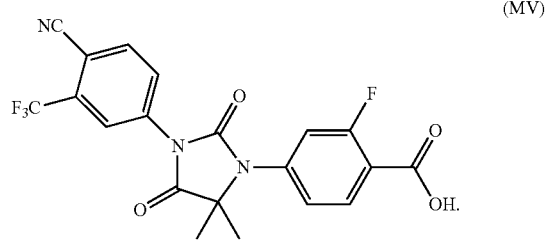 [SMILES: CC1(C)C(=O)N(c2ccc(C#N)c(C(F)(F)F)c2)C(=O)N1c1ccc(C(=O)O)c(F)c1]

(MV)

* * * * *